(12) United States Patent
Turkson et al.

(10) Patent No.: US 9,802,888 B2
(45) Date of Patent: Oct. 31, 2017

(54) STAT3 INHIBITORS

(71) Applicants: UNIVERSITY OF HAWAII, Honolulu, HI (US); THE GOVERNING COUNCIL OF THE UNIVERSITY OF TORONTO, Toronto (CA)

(72) Inventors: James Turkson, Honolulu, HI (US); Patrick Gunning, Toronto (CA); Sina Haftchenary, Toronto (CA)

(73) Assignee: UNIVERSITY OF HAWAII, Honolulu, HI (US)

( * ) Notice: Subject to any disclaimer, the term of this patent is extended or adjusted under 35 U.S.C. 154(b) by 0 days.

(21) Appl. No.: 14/779,276

(22) PCT Filed: Mar. 21, 2014

(86) PCT No.: PCT/US2014/031412
§ 371 (c)(1),
(2) Date: Sep. 22, 2015

(87) PCT Pub. No.: WO2014/153495
PCT Pub. Date: Sep. 25, 2014

(65) Prior Publication Data
US 2016/0068478 A1 Mar. 10, 2016

Related U.S. Application Data

(60) Provisional application No. 61/804,613, filed on Mar. 22, 2013.

(51) Int. Cl.
*C07C 311/18* (2006.01)
*C07C 311/19* (2006.01)

(52) U.S. Cl.
CPC .......... *C07C 311/18* (2013.01); *C07C 311/19* (2013.01); *C07C 2601/14* (2017.05)

(58) Field of Classification Search
CPC .................... C07C 311/18; C07C 2101/14
See application file for complete search history.

(56) References Cited

U.S. PATENT DOCUMENTS

| 3,773,919 A | 11/1973 | Boswell et al. | |
| 2005/0158894 A1* | 7/2005 | Ohba | G09F 9/35 438/22 |
| 2011/0275577 A1 | 11/2011 | Priebe et al. | |
| 2014/0275187 A1 | 9/2014 | Rubin et al. | |

FOREIGN PATENT DOCUMENTS

| WO | WO2007042912 | 4/2007 | |
| WO | WO2009100121 | 8/2009 | |
| WO | WO2010118309 | 10/2010 | |
| WO | WO2011163424 | 12/2011 | |
| WO | WO 2013177534 A2 * | 11/2013 | ........... C07D 215/36 |

OTHER PUBLICATIONS

Haftchenary et al. ACS Med. Chem. Lett. (2013), 4(11), p. 1102-1107.*
Zhang et al. PNAS, 109(2012), p. 9623-9628 (disclosed in IDS).*
Bowman et al., STATs in oncogenesis. Oncogene 19:2474-2488 (2000).
Bromberg, Signal transducers and activators of transcription as regulators of growth, apoptosis and breast development. Breast Cancer Res. 2:86-90 (2000).
Bromberg et al., The role of STATs in transcriptional control and their impact on cellular function, Oncogene 19:2468-2473 (2000).
Catlett-Falcone et al., Constitutive activation of Stat3 signaling confers resistance to apoptosis in human U266 myeloma cells; Immunity 10:105-115 (1999).
Chi et al., Physical Stability of Proteins in Aqueous Solution: Mechanism and Driving Forces in Nonnative Protein Aggregation, Pharm. Res., 20(9): 1325-36 (2003).
Cleland et al., The Development of Stable Protein Formulations: A Close Look at Protein Aggregation, Deamidation, and Oxidation, Crit. Rev. Ther. Drug Carrier Syst., 70(4):307-77 (1993).
Coleman et al., Investigation of the binding determinants of phosphopeptides targeted to the SRC homology 2 domain of the signal transducer and activator of transcription 3. Development of a high-affinity peptide inhibitor. J Med Chem. 48(6661-70) (2005).
Darnell, Transcription factors as targets for cancer therapy, Nat. Rev. Cancer 2:740-749 (2002).
During et al., Controlled Release of Dopamine from a Polymeric Brain Implant: In Vivo Characterization, Ann. Neurol. 25:351 (1989).
Garcia et al., Constitutive activation of Stat3 by the Src and JAK tyrosine kinases participates in growth regulation of human breast carcinoma cells, Oncogene 20:2499-2513 (2001).
Goodson, in Medical Applications of Controlled Release, supra, vol. 2, pp. 115-138 (1984).
Gough et al., Mitochondrial STAT3 Supports Ras-Dependent Oncogenic Transformation. Science 324:1713 (2009).
Gouilleux et al., Prolactin and interleukin-2 receptors in T lymphocytes signal through a MGF-STAT5-like transcription factor. Endocrinology 136:5700-5708 (1995).
Gritsko et al., Persistent activation of stat3 signaling induces survivin gene expression and confers resistance to apoptosis in human breast cancer cells, Clin Cancer Res. 12:11-9 (2006).
Grivennikov et al., Dangerous liaisons: STAT3 and NF-kB collaboration and crosstalk in cancer, Cytokine & Growth Factor Reviews 21:11-19 (2010).
Howard et al., Intracerebral drug delivery in rats with lesion-induced memory deficits, J. Neurosurg. 71:105 (1989).
Johnson et al., Overexpressed pp60$^{c-src}$ can induce focus formation without complete transformation of NIH 3T3 cells. Mol. Cell. Biol. 5:1073-1083 (1985).
Konigsmann et al., Fludarabine and Bendamustine in Refractory and Relapsed Indolent Lymphoma—a Multicenter Phsae I/II Trial of the East German Society of Hematology and Oncology (OSHO), Leuk Lymphoma. 45 (9): 1821-1827 (2004).
Langer, New Methods of Drug Delivery, Science 249:1527-1533 (1990).

(Continued)

Primary Examiner — Yong Chu
(74) Attorney, Agent, or Firm — Duane Morris LLP; Vicki G. Norton

(57) ABSTRACT

The present disclosure provides pharmaceutical compositions comprising Stat3 inhibitors and certain pharmaceutically acceptable salts thereof, and methods of use.

11 Claims, 24 Drawing Sheets

(56) References Cited

OTHER PUBLICATIONS

Levy et al., Inhibition of Calcification of Bioprosthetic Heart Valves by Local Controlled-Release Diposhphonate, Science 228:190 (1985).
Miklossy et al., Therapeutic modulators of STAT signaling for human diseases. Nat Rev Drug Discov 12:611-629 (2013).
Mora et al., Constitutive activation of Stat3 in human prostate tumors and cell lines: direct inhibition of Stat3 signaling induces apoptosis of prostate cancer cells, Cancer Res 62:6659-66 (2002).
Nicolaou et al., Calicheamicin $\theta^1{}_1$: A Rationally Designed Molecule with Extremely Potent and Selective DNA Cleaving Properties and Apoptosis Inducing Activity, Angew Chem. Intl. Ed. Engl. 33:183-186 (1994).
Niu et al., Constitutive Stat3 activity up-regulates VEGF expression and tumor angiogenesi, Oncogene 21:2000-2008 (2002).
Niu et al., Roles of activated Src and Stat3 signaling in melanoma tumor cell growth, Oncogene 21:7001-7010 (2002).
Ranger et al., Chemical and Physical Structure of Polymers as Carriers for Controlled Release of Bioactive Agents: A Review, J. Macromol. Sci. Rev. Macromol. Chem. 23:61 (1983).
Saudek et al., A Preliminary Trial of the Programmable Implantable Medication System for Insulin Delivery, N. Engl. J. Med. 321:574 (1989).
Sefton, Implantable Pumps, CRC Crit. Ref. Biomed. Eng. 14 (3):201 (1987).
Shuai et al., Interferon activation of the transcription factor Stat91 involves dimerization through SH2-phosphotyrosyl peptide interactions. Cell 76:821-828 (1994).
Siddiquee et al., Selective chemical probe inhibitor of Stat3, identified through structure-based virtual screening, induces antitumor activity, Proc Natl Acad Sci U S A. 104:7391-7396 (2007).
Siddiquee et al., An Oxazole-Based Small-Molecule Stat3 Inhibitor Modulates Stat3 Stability and Processing and Induces Antitumor Cell Effects. ACS Chem. Biol. 2:787-798 (2007).
Siddiquee et al., STAT3 as a target for inducing apoptosis in solid and hematological tumors, Cell Res. 18:254-267 (2008).
Sidman et al., Controlled Release of Macromolecules and Pharmaceuticals from Synthetic Polypeptides Based on Glutamic Acid, Biopolymers, 22:547-556 (1983).
Song et al., A low-molecular-weight compound discovered through virtual database screening inhibits Stat3 function in breast cancer cells, Proc Natl Acad Sci U S A. 102:4700-5 (2005).
Thomas, Authorized Officer, U.S., International Search Report and Written Opinion, International Application No. PCT/US2014/031412, 12 pages (2014).
Tsukuda et al., Phase I trial of combined chemotherapy with docetaxel, cisplatin, and 5-fluorouacil for patients with locally advanced squamous cell carcinoma of the head and neck, Int J Clin Oncol., 9 (3): 161-6 (2004).
Turkson et al., STAT proteins: novel molecular targets for cancer drug discovery. Oncogene 19:6613-6626 (2000).
Turkson, STAT proteins as novel targets for cancer drug discovery. Expert Opin Ther Targets 8:409-422 (2004).
Turkson et al., A novel platinum compound inhibits constitutive Stat3 signaling and induces cell cycle arrest and apoptosis of malignant cells. J Biol Chem. 280:32979-32988 (2005).
Turkson et al., Requirement for Ras/Rac1-Mediated p38 and c-Jun N-Terminal Kinase Signaling in Stat3 Transcriptional Activity Induced by the Src Oncoprotein. Mol. Cell. Biol. 19:7519-7528 (1999).
Turkson et al., Stat3 activation by Src induces specific gene regulation and is required for cell transformation. Mol. Cell. Biol. 18:2545-2552 (1998).
Turkson et al., Phosphotyrosyl peptides block Stat3-mediated DNA-binding activity, gene regulation and cell transformation. J. Biol. Chem. 276:45443-45455 (2001).
Turkson et al., Novel peptidomimetic inhibitors of signal transducer and activator of transcription 3 dimerization and biological activity, Mol Cancer Ther 3:261-269 (2004).
Wagner et aL, The SIF binding element confers sis/PDGF inducibility onto the c-fos promoter. EMBO J. 9:4477-4484 (1990).
Wang, Instability, stabilization, and formulation of liquid protein pharmaceuticals, Int. J. Pharm., 7S5(2): 129-88 (1999).
Wang, Lyophilization and development of solid protein pharmaceuticals, Int. J. Pharm., 203(1-2): 1-60 (2000).
Wang et al., Regulation of the innate and adaptive immune responses by Stat-3 signaling in tumor cells. Nat Med 10:48-54 (2004).
Wei et al., Stat3 activation regulates the expression of vascular endothelial growth factor and human pancreatic cancer angiogenesis and metastasis, Oncogene 22:319-29 (2003).
Xie et al., Stat3 activation regulates the expression of matrix metalloproteinase-2 and tumor invasion and metastasis, Oncogene 23:3550-60 (2004).
Yu et al., The STATS of Cancer—New molecular targets come of age, Nat. Rev. Cancer 4:97-105 (2004).
Yu et al., STATs in cancer inflammation and immunity: a leading role for STAT3. Nat Rev Cancer 9:798-809 (2009).
Yu et al., Enhanced DNA-binding activity of a Stat3-related protein in cells transformed by the Src oncoprotein. Science 269:81-83 (1995).
Yue et al., Targeting STAT3 in cancer: how successful are we?, Expert Opin Investig Drugs. 18:45-56 (2009).
Zhang et al., Orally bioavailable small-molecule inhibitor of transcription factor Stat3 regresses human breast and lung cancer xenografts. Proc Natl Acad Sci U S A 109:9623-8 (2012).
Zhang et al., A novel small-molecule disrupts Stat3 SH2 domain-phosphotyrosine interactions and Stat3-dependent tumor processes. Biochem Pharmacol 79:1398-409 (2010).
Buchwald et al., Long-term, continuous intravenous heparin administration by an implantable infusion pump in ambulatory patients with recurrent venous thrombosis, Surgery, 507-516 (1980).

\* cited by examiner

Table 1. Intracellular levels of SH5-07

| Treated time with 5 μM of SH5-07 | SH5-07 concentration in cell lysate (nM) |
|---|---|
| Untreated (DMSO) control | 5.6 ± 5.1 |
| Treated cells, 1 h | 1236.3 ± 181.0 |
| Treated cells, 6 h | 27.6 ± 13.3 |
| Treated cells, 24 h | 1.0 ± 0.9 |

FIG. 10

STAT3 INHIBITORS

RELATED APPLICATIONS

This application is a 35 U.S.C. §371 U.S. National Phase Application of International Application No. PCT/US14/31412, filed on Mar. 21, 2014, which claims the benefit of priority of U.S. Provisional Patent Application No. 61/804,613, filed on Mar. 22, 2013, each of which is incorporated herein by reference in their entirety.

GOVERNMENT RIGHTS

This invention was made with government support under Grant numbers R01 CA128865 and R01 CA161931 awarded by the National Institutes of Health. The Government has certain rights in this invention.

FIELD

The present disclosure is generally related to novel, potent and selective Stat3 inhibitors of formula I and pharmaceutically acceptable salts thereof. The present disclosure also relates to pharmaceutical compositions containing the inhibitors and their use in the treatment or prevention of cancer, and other pathogenic conditions in which STAT-3 activation is implicated. As an example, the disclosure provides methods and compositions for the treatment of cancer by modulating STAT-3.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

The signal transducer and activator of transcription (Stat) family of proteins are cytoplasmic transcription factors with important roles in mediating responses to cytokines and growth factors, including promoting cell growth and differentiation, and inflammation and immune responses. Bromberg, Signal transducers and activators of transcription as regulators of growth, apoptosis and breast development. Breast Cancer Res. 2:86-90 (2000); Darnell, Transcription factors as targets for cancer therapy, Nat. Rev. Cancer 2:740-749 (2002). Classically, the phosphorylation of Stats on a critical tyrosyl residue by growth factor receptor tyrosine kinases, or cytoplasmic tyrosine kinases, including Janus kinases or the Src family kinases, promotes the dimerization between two Stat monomers through a reciprocal phosphotyrosine-Src Homology (SH)2 domain interaction, translocation to the nucleus, and the binding to specific DNA-response elements in the promoters of target genes to regulate gene expression. By contrast, aberrantly-active Stat3, one of the Stat family members, has been implicated in many human tumors and represents an attractive target for drug discovery. The aberrant activation of Stat3 occurs in glioma, breast, prostate, ovarian, and many other human cancers, whereby it promotes malignant progression. Yu & Jove, The STATS of Cancer-New molecular targets come of age, Nat. Rev. Cancer 4:97-105 (2004); Yue & Turkson, Targeting STAT3 in cancer: how successful are we?, Expert Opin Investig Drugs. 18:45-56 (2009). Mechanisms by which constitutively-active Stat3 mediates tumorigenesis include dysregulation of gene expression that leads to uncontrolled growth and survival of tumor cells, enhanced tumor angiogenesis, and metastasis and the suppression of tumor immune surveillance. Yu & Jove (2004); Bromberg & Darnell, The role of STATs in transcriptional control and their impact on cellular function, Oncogene 19:2468-2473 (2000); Bowman et al., STATs in oncogenesis. Oncogene 19:2474-2488 (2000); Turkson J & Jove, STAT proteins: novel molecular targets for cancer drug discovery. Oncogene 19:6613-6626 (2000); Turkson, STAT proteins as novel targets for cancer drug discovery. Expert Opin Ther Targets 8:409-422 (2004); Wang et al., Regulation of the innate and adaptive immune responses by Stat-3 signaling in tumor cells. Nat Med 10:48-54 (2004).

Recent evidence also reveals the role of Stat3 in modulating mitochondrial functions and Stat3 crosstalk with other proteins, such as NF-κB, that promotes the malignant phenotype. Many human tumors harbor aberrantly-active signal transducer and activator of transcription (Stat)3 signaling, and studies in experimental models indicate tumor cells and tumors harboring constitutively-active Stat3 are responsive to Stat3 signaling modulators. See Gough et al., Mitochondrial STAT3 Supports Ras-Dependent Oncogenic Transformation. Science 324:1713 (2009); Yu et al., STATs in cancer inflammation and immunity: a leading role for STAT3. Nat Rev Cancer 9:798-809 (2009); Grivennikov & Karin, Dangerous liaisons: STAT3 and NF-kB collaboration and crosstalk in cancer, Cytokine & Growth Factor Reviews 21:11-19 (2010).

SUMMARY OF THE INVENTION

In one aspect, this invention relates to novel, selective and potent Stat 3 inhibitors, useful as cancer therapeutics. In some aspects, the compounds of this invention are useful for inhibiting malignant transformation, tumor development and progression.

In one aspect, this invention relates to compounds of Formula I, which selectively inhibit Stat3.

FORMULA I

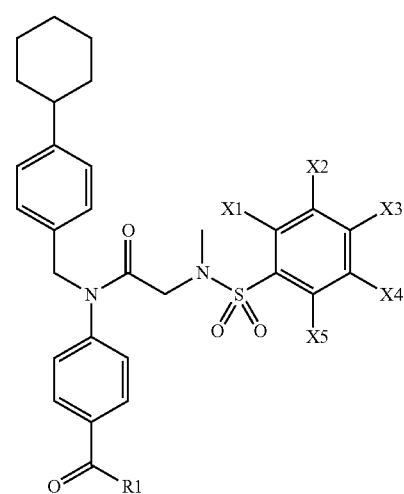

Formula (I)

In one aspect, X1 to X5 are independently halogen (e.g., F, Cl, I, or Br) or H, and R₁ is selected from the group consisting of —NH—OH or —OR₂, where R₂ is selected from H or lower alkyl. In some embodiments X1 to X5 are F, and $R_1$ is selected from —NH—OH or —$OR_2$ where $R_2$ is H, as, for example, as shown in Formulas II (SH5-07) and Formula III:

Formula II

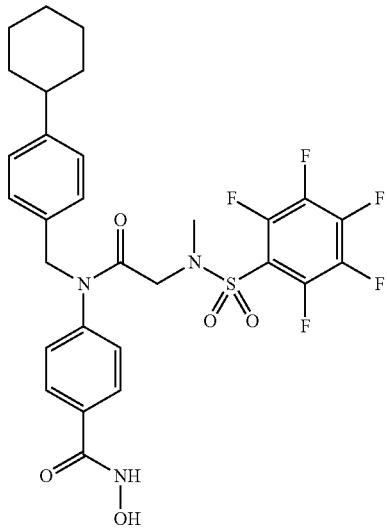

SH5-07

Formula III

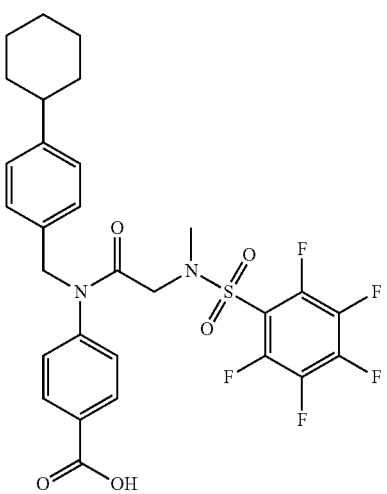

SH4-54

In some embodiments, when X1 to X5 are F, and $R_1$ is —$OR_2$, $R_2$ is not ethyl.

In one aspect, the compounds of this invention inhibit Stat3 while exhibiting little or no inhibition of Stat1 or Stat 5 at concentrations of at least twice the IC50 for Stat 3 inhibition. The compounds of this invention uniquely interact with three sub-pockets on the stat3:stat3 dimer interface, in contrast to other previously described Stat3 inhibitors, which interacts with only two sub-pockets. As a result of the uniqe and specific mechanism by which the inhibitors of this invention exert their effects, the compounds are more potent and less toxic. The compounds of this invention also suprisingly selectively bind inhibit the activated form of Stat3, consequently attenuating Stat3 functions in cancer cells. The compounds of this invention are useful, for example, for inhibiting cancer cell growth, survival, migration and/or metastasis.

In one aspect, this invention relates to compounds such as SH5-07 and SH4-54, which preferentially inhibit Stat3 DNA-binding activity with IC50s of 4 µM or less, but exhibit little or no disruption of Stat1 or Stat5 DNA-binding activity at concentrations up to 20 µM. In one aspect, this invention relates to compositions and formulations useful for inhibiting cancer growth. In some aspects, the anti-cancer activity of the compounds can be determined by the ability to inhibit growth of mouse xenografts of human breast and non-small cell lung cancers.

Dimerization of Stat3 occurs through SH2-phosphotyrosyl peptide interactions. See Shuai et al., Interferon activation of the transcription factor Stat91 involves dimerization through SH2-phosphotyrosyl peptide interactions. Cell 76:821-828 (1994); Miklossy et al. Therapeutic modulators of STAT signaling for human diseases. Nat Rev Drug Discov 12:611-629 (2013); 15-23 Turkson et al., Novel peptidomimetic inhibitors of signal transducer and activator of transcription 3 dimerization and biological activity, Mol Cancer Ther 3:261-269 (2004); Turkson et al., Phosphotyrosyl peptides block Stat3-mediated DNA-binding activity, gene regulation and cell transformation. J. Biol. Chem. 276: 45443-45455 (2001); Siddiquee et al., Selective chemical probe inhibitor of Stat3, identified through structure-based virtual screening, induces antitumor activity, Proc Natl Acad Sci USA. 104:7391-7396 (2007). Siddiquee KAZ, STAT3 as a target for inducing apoptosis in solid and hematological tumors, Cell Res. 18:254-267 (2008); Siddiquee et al., An Oxazole-Based Small-Molecule Stat3 Inhibitor Modulates Stat3 Stability and Processing and Induces Antitumor Cell Effects. ACS Chem. Biol. 2:787-798 (2007); Coleman et al., Investigation of the binding determinants of phosphopeptides targeted to the SRC homology 2 domain of the signal transducer and activator of transcription 3. Development of a high-affinity peptide inhibitor. J Med Chem. 48(6661-70) (2005).

In one aspect, the invention relates to the inventors' design of Stat3 inhibitors which interfere with the dimerization between two monomers, and the inventors' recognition that this represents an attractive strategy to develop drugs that inhibit Stat3 activation and functions.

BP-1-102 was previously reported to have Stat 3 inhibitory activity. See Zhang et al., Orally bioavailable small-molecule inhibitor of transcription factor Stat3 regresses human breast and lung cancer xenografts. Proc Natl Acad Sci USA 109:9623-8 (2012). In the present invention, structural information from the computational modeling of BP-1-102 bound to the Stat3 SH2 domain was used by the inventors herein to design novel Stat3 inhibitors, such as the compounds of Formula I, which include exemplary analogs, SH5-07 and SH4-54. As shown in Formulas II and III, SH5-07 and SH4-54 comprise hydroxamic and carboxylic acid moieties, respectively, with $IC_{50}$ values of around 3.3 µM, or less. In one aspect, this invention relates to the design and characterization of SH5-07 as an orally-bioavailable Stat3 inhibitor in vitro and in vivo. The compounds of this invention surprisingly show improved Stat3-inhibitory activity compared to inhibitors with a salicylic acid moiety. For example, the compounds of this invention have IC50's or activities that are two to ten times less than BP-1-102.

The present disclosure provides novel, selective STAT-3 inhibitors, and pharmaceutical formulations and kits comprising the inhibitors. The compounds and pharmaceutical formulations are useful as therapeutics for cancer and other conditions mediated by aberrantly active STAT-3, a substrate for growth factor receptor tyrosine kinases, or cytoplasmic tyrosine kinases, including Janus kinases or the Src family kinases. In some aspects, the processes inhibited by the compounds and compositions of this invention include proliferation, survival, angiogenesis, migration/metastasis/invasion, and immunity.

The compounds of this invention are useful for inhibiting activities resulting from constitutive STAT-3 activation, which include: a) stimulating proliferation by increasing the expression of c-Myc and/or cyclin D1/D2, and/or decreasing expression of p53; b) increasing survival by increasing the expression of survivin, Bcl-x/Bcl-2, Mcl-1 and/or Akt-2; stimulating angiogenesis by increasing expression of VEGF; and/or increasing migration/metastasis or invasion by increasing the expression MMP-2 or MMP-9.

The compounds of Formulas I-III can be used in the compositions and methods of this invention as described herein.

In one aspect, the present disclosure provides the use of a compound of any of formulas I-III for the preparation of a medicament for the treatment of a condition selected from the group consisting of cancer, hyperplasia, and neoplasia. In one embodiment, the tumor progression, including metastasis and/or growth is thereby inhibited and/or reduced. In one embodiment, multi-drug resistance is thereby inhibited and/or reduced.

In another aspect the present disclosure provides a method of treating cancer comprising administering to a subject in need thereof a therapeutically effective amount of a pharmaceutical composition comprising a compound of any of Formulas I-III, whereby the cancer is treated, cancer progression is stopped or slowed, and/or STAT-3 is inhibited.

In one embodiment, the level of STAT-3 activity is reduced in cancer cells. In one aspect, the effective dose of the STAT-3 inhibitor is administed at a dose ranging from 0.05 mg/kg to 4 mg/kg. The therapeutically effective dose may be, for example, about 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, or about 4.0 mg/kg, or any range in between any two of the recited doses. In some embodiments the dose will be 0.08 mg/kg to about 0.5 mg/kg, from about 0.08 to about 0.24 mg/kg, or from about 0.24 to about 0.5 mg/kg. In another aspect, the effective dose of the STAT-3 inhibitor is given in one or more doses. For example, a therapeutically of, for example, 0.08, 0.24, or 0.5 mg/kg for each dose. In one embodiment, the dose is administered by a delivery route selected from the group consisting of intraperitoneal, intradermal, intramuscular, intraperitoneal, intravenous, topical, subcutaneous, intranasal, or epidural routes. In one embodiment, the one or more effective doses of the STAT-3 inhibitor are administered orally, intravenously, intramuscularly, or subcutaneously. In one embodiment, the one or more effective doses of the STAT-3 inhibitor are administered orally. In one embodiment, the one or more effective doses of the STAT-3 inhibitor are administered intravenously. In certain embodiments, the one or more effective doses of the STAT-3 inhibitor are administered subcutaneously. In one embodiment, the one or more effective doses of the STAT-3 inhibitor are administered intramuscularly.

In one aspect, this disclosure provides a method of treatment comprising administering to a subject in need thereof an effective amount of a pharmaceutical composition comprising a Stat3 inhibitor of this invention. In one embodiment, the subject has a glioma, breast cancer, or pancreatic cancer. In some embodiments, the subject has a solid tumor cancer. In another aspect, the solid tumor comprises sarcomas, carcinomas or lymphomas. In one embodiment, the cancer is selected from the group consisting of: brain tumors, such as gliomas, medulloblastomas, cerebral menangiomas, breast, prostate, pancreatic, ovarian, bladder, head and neck, malignant melanoma, multiple myeloma, lymphomas, including anaplastic large T cell lymphoma, sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous lekemia (CML), megakaryocytic leukemia, and large granula lymphocyte (LGL) leukemia, or thyroid, skin, lung, or kidney cancer. In some embodiments the cancer may be renal cell carcinoma, pancreatic adenocarcinoma, ovarian carcinoma, suamous cell carcinoma of the head and neck, or Hodgkin's Lymphoma.

According to one aspect of the present invention, there are provided novel compositions comprising compounds represented by Formulas I-III, their pharmaceutically acceptable salts, and pharmaceutical compositions containing them, or mixture thereof.

The inventions described and claimed herein have many attributes and embodiments, including, but not limited to, those set forth, or described, or referenced, in this Brief Summary. It is not intended to be all-inclusive and the inventions described and claimed herein are not limited to, or by the features or embodiments identified in, this Brief Summary, which is included for purposes of illustration only and not restriction. Additional embodiments may be disclosed in the Detailed Description below.

BRIEF DESCRIPTION OF THE FIGURES

FIG. 1 (A) shows structures of SH5-07 and SH4-54; (B and C) Nuclear extracts of equal total protein containing activated Stat3 (B) or Stat1 and Stat5 (C) were pre-incubated with or without increasing concentration of SH5-07 or SH4-54 for 30 min at room temperature prior to the incubation with the radiolabeled (C) hSIE probe that binds Stat3 or (B) MGFe probe that binds Stat1 and Stat5 and subjecting to EMSA analysis. Positions of STATs:DNA complexes are labeled; control lanes (0) represent nuclear extracts treated with 0.05% DMSO. Data are representative of 3-4 independent determinations.

FIG. 2 (H). Another examplar of intracellular levels of Stat3 activation. FIG. 2 (I). Another example of concentration dependent inhibition of Stat3 phosphorylation inside exemplary tumor cells by the stat 3 inhibitors of this disclosure. 2 (J) Another example of time-dependent inhibition of stat3 phosphorylation inside tumor cells.

FIG. 5 (H). Another example of the efficacy and selective inhibition by SH507 in tumor cell viability. FIG. 5(I). Exemplary assay for the determination of IC50 value using SH4-54 and MDA-MB-231 cell lines.

FIG. 10. Table showing representative intracellular levels of SH5-07.

DETAILED DESCRIPTION

Figure 1:
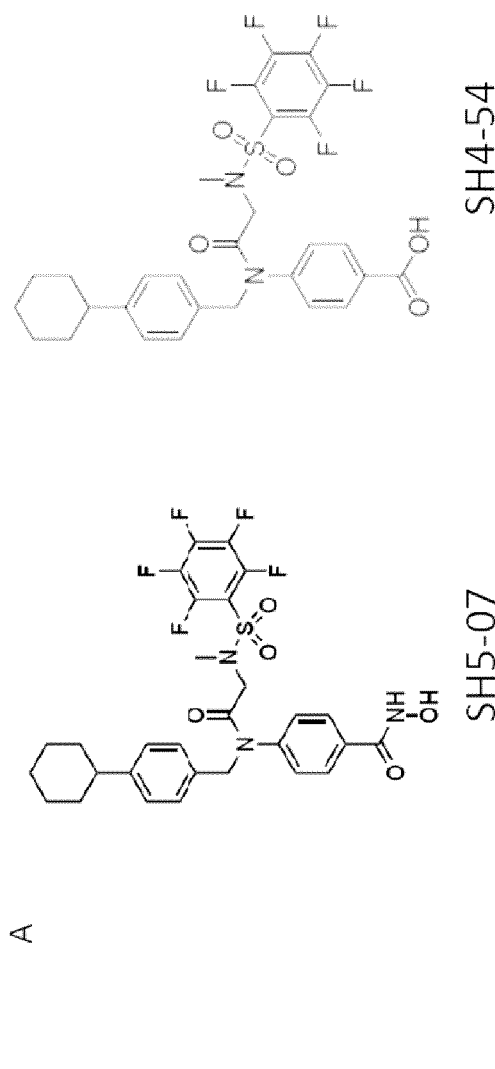
FIG. 1. Chemical structures of SH5-07 and SH4-54 and their inhibitory activities against STAT DNA-binding activities.
Figure 1:
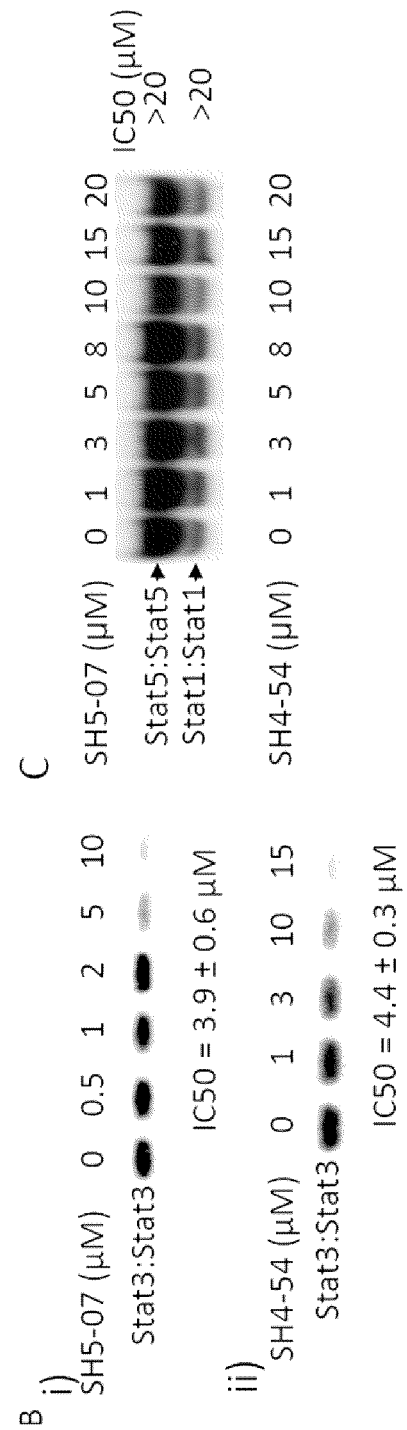

The present disclosure relates generally to novel, potent and selective Stat3 inhibitors. Constituitively activated Stat3 has been found to play a role in cancerous cells and the substantially faster proliferation, invasiveness and rate of cancerous cells compared to cells of the non-cancerous origin. In some embodiments, the selective Stat3 inhibitors of this invention can suppress cancer cell growth, proliferation, survival, angiogenesis, migration/invasion and/or immunity. The inhibition of Stat3 can be achieved by inhibiting dimerization of Stat3.

Stat3:Slat3 protein complexes are mediated through reciprocal pTyr705SH2 domain interactions. Most drugs targeting Stat3 include a phosphoryl group to mimic pTyr705. While the phosphate functionality is regarded as being essential to targeting the SH2 domain, it is unsuitable for drug discovery as it suffers from poor cell permeability and metabolic degradation. As described herein, it was suprisingly found that the compounds of Formulas I-III are highly potent Stat3 inhibitors with nanomolar potency against some of the most aggressive brain cancer cells identified to this date.

The prevalence of constitutively-active Stat3 in human tumors places an increasing importance on the discovery of suitable Stat3-inhibitors as novel anticancer drugs; however, although many Stat3 inhibiting modalities have been reported, no Stat3 small-molecule inhibitor drug has yet reached to the clinic. Miklossy et al., Therapeutic modulators of STAT signaling for human diseases. Nat Rev Drug Discov 12:611-629 (2013). As described herein, compounds of Formulas I-III, for example, SH5-07 and SH4-54 (the hydroxamic and benzoic acid derivatives, respectively, of the previously reported inhibitor of Stat3, BP-1-102), show a 2-fold improved Stat3-inhibitory potency in vitro. It is notable that both agents induce preferential antitumor cell response in vitro against human glioma tumor cells. As described herein, the compounds also show antitumor cell responses to breast cancer and pancreatic or prostate cancer cells or the v-Src-transformed mouse fibroblasts at low micromolar concentrations. Further, SH5-07 exhibited improved target selectivity and showed a minimum inhibitory effect on the phosphorylation of Src, Jak2, Shc, ERK1/2$^{MAPK}$, or Akt at concentrations (3-10 μM) that inhibit intracellular Stat3 activation, despite there being SH2 domains involved in the mechanisms leading to the activation of these other proteins.

Substantive evidence demonstrates that aberrant Stat3 activity promotes cancer cell growth and survival, and induces tumor angiogenesis and metastasis Inhibitors of Stat3 activation promote antitumor cell effects, although many of these have low potencies. See Turkson et al., Novel peptidomimetic inhibitors of signal transducer and activator of transcription 3 dimerization and biological activity, Mol Cancer Ther 3:261-269 (2004); Turkson et al., Phosphotyrosyl peptides block Stat3-mediated DNA-binding activity, gene regulation and cell transformation, J. Biol. Chem. 276:45443-45455 (2001); Garcia et al., Constitutive activation of Stat3 by the Src and JAK tyrosine kinases participates in growth regulation of human breast carcinoma cells, Oncogene 20:2499-2513 (2001); Catlett-Falcone et al., Constitutive activation of Stat3 signaling confers resistance to apoptosis in human U266 myeloma cells; Immunity 10:105-115 (1999); Mora et al., Constitutive activation of Stat3 in human prostate tumors and cell lines: direct inhibition of Stat3 signaling induces apoptosis of prostate cancer cells, Cancer Res 62:6659-66 (2002); Niu et al., Constitutive Stat3 activity up-regulates VEGF expression and tumor angiogenesi, Oncogene 21:2000-2008 (2002); Wei et al., Stat3 activation regulates the expression of vascular endothelial growth factor and human pancreatic cancer angiogenesis and metastasis, Oncogene 22:319-29 (2003); Xie et al., Stat3 activation regulates the expression of matrix metalloproteinase-2 and tumor invasion and metastasis, Oncogene 23:3550-60 (2004).

The present disclosure is based on the surprising discovery that certain structurally distinct analogs of previously reported Stat3 inhibitors had unexpected and potentiated therapeutic activity. SH5-07 shows more improved potency in vitro compared to BP-1-102 and many of the reported small-molecule Stat3 inhibitors in suppressing viability, colony survival, and migration of human breast cancer and glioma cells harboring constitutively-active Stat3. Mechanistic insight into the biological effects of SH5-07 as a Stat3 inhibitor is provided by the evidence disclosed herein of suppression of the constitutive expression of genes regulated by Stat3 genes, including Bcl-2, Bcl-xL, Cyclin D1, c-Myc, and Survivin, which control cell growth and survival. Song et al., A low-molecular-weight compound discovered through virtual database screening inhibits Stat3 function in breast cancer cells, Proc Natl Acad Sci USA. 102:4700-5 (2005); Zhang et al., Orally bioavailable small-molecule inhibitor of transcription factor Stat3 regresses human breast and lung cancer xenografts, Proc Natl Acad Sci USA 109: 9623-8 (2012); Catlett-Falcone et al., Constitutive activation of Stat3 signaling confers resistance to apoptosis in human U266 myeloma cells, Immunity 10:105-115 (1999); Gritsko et al., Persistent activation of stat3 signaling induces survivin gene expression and confers resistance to apoptosis in human breast cancer cells, Clin Cancer Res. 12:11-9 (2006). Altogether the present study provides evidence for the inhibition of constitutively-active Stat3 in malignant cells that lead to antitumor cell effects against human breast cancer and glioma cells in vitro.

Definitions

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur, or phosphorous, atoms replacing one or more carbons of the hydrocarbon backbone. The term "aromatic-alkyl" includes alkyl groups substituted with one or more aryl groups. The term "lower alkyl" as used herein refers to 4 or fewer carbons.

The term "aryl" includes groups with aromaticity, including 5- and 6-membered single-ring aromatic groups that may include from zero to four heteroatoms, as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused, or bridged, with alicyclic or heterocyclic rings which are not aromatic, so as to form a multicyclic system (e.g., tetralin, methylenedioxyphenyl).

The term "alkylene" refers to divalent saturated aliphatic groups and includes both straight chain and branched chain groups.

The term "alkenylene" refers to divalent aliphatic groups having a double bond and includes both straight chain and branched chain groups.

As used herein, a "subject" refers to an animal that is the object of treatment, observation or experiment. "Animal" includes cold- and warm-blooded vertebrates and invertebrates, such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating, or controlling.

As used herein, the term "treating" refers to both therapeutic treatment and prophylactic, or preventative, measures, or administering an agent suspected of having therapeutic potential. The term includes preventative (e.g., prophylactic) and palliative treatment.

The term "a pharmaceutically effective amount", as used herein, means an amount of active compound, or pharmaceutical agent, that elicits the biological, or medicinal, response in a tissue, system, animal, or human that is being sought, which includes alleviation or palliation of the symptoms of the disease being treated and/or an amount sufficient to have utility and provide desired therapeutic endpoint. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression and/or determining the response rate.

The term "pharmaceutically acceptable", as used herein, means that the substance or composition must be compatible chemically and/or toxicologically, with the other ingredients comprising a formulation, and/or the mammal being treated therewith.

The term "cancer" refers to, or describes, the physiological condition in mammals that is typically characterized by unregulated cell growth and/or hyperproliferative activities. A "tumor" comprises one or more cancerous cells. Examples of cancer include, but are not limited to, carcinoma, lymphoma, blastoma, sarcoma, and leukemia or lymphoid malignancies. In one embodiment, the cancer is a solid tumor. More particular examples of such cancers include breast cancer, cervical cancer, ovarian cancer, bladder cancer, endometrial or uterine carcinoma, prostate cancer, glioma and other brain or spinal cord cancers, squamous cell cancer (e.g., epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, liver cancer, hepatoma, colon cancer, rectal cancer, colorectal cancer, salivary gland carcinoma, kidney or renal cancer, vulval cancer, thyroid cancer, hepatic carcinoma, anal carcinoma, penile carcinoma, as well as head and neck cancer. In one embodiment, the treatment comprises treatment of solid tumors. In one embodiment, the tumors comprises sarcomas, carcinomas or lymphomas.

In some embodiments, the cancer is selected from the group consisting of: brain tumors, such as gliomas, medulloblastomas, cerebral menangiomas, pancreatic cancer, malignant melanoma, multiple myeloma, lymphomas, including anaplastic large T cell lymphoma, sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous lekemia (CML), megakaryocytic leukemia, and large granula lymphocyte (LGL) leukemia, thyroid cancer, brain cancer, skin cancer, lung cancer, and kidney cancer. In some embodiments the cancer may be renal cell carcinoma, pancreatic adenocarcinoa, ovarian carcinoa or Hodgkin Lymphoma.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: trastuzumab (HERCEPTIN®, Genentech), erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum (II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), temozolomide (4-methyl-5-oxo-2,3,4,6,8-pentazabicyclo[4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCINO), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXA- VAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaII (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate, or inhibit, hormone action on tumors, such as anti-estrogens and selective estrogen receptor modulators (SERMs), including, e.g., tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, e.g., 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, e.g., PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, e.g., ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents, in combination with the gamma-glutamyl inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound, or salt thereof. Metabolites of a compound may be identified using routine techniques known in the art, and their activities determined, using tests such as those described herein. Such products may result e.g., from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic, or inorganic, salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule, such as an acetate ion, a succinate ion, or other counter ion. The counter ion may be any organic, or inorganic, moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, e.g., treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, e.g., treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association, or complex, of one or more solvent molecules and a compound of the invention. Examples of solvents that form solvates include, but are not limited to, water, isopropanol, ethanol, methanol, DMSO, ethylacetate, acetic acid, and ethanolamine.

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), intraperitoneal (IP), transdermal, rectal, nasal, topical (including buccal and sublingual), vaginal, intrapulmonary and intranasal. For local treatment, the compounds may be administered by intratumor administration, including perfusing or otherwise contacting the tumor with the inhibitor. It will be appreciated that the preferred route may vary with, e.g., the condition of the recipient. Where the compound is administered orally, it may be formulated as a pill, capsule, tablet, etc., with a pharmaceutically acceptable carrier or excipient. Where the compound is administered parenterally, it may be formulated with a pharmaceutically acceptable parenteral vehicle, and in a unit dosage injectable form, as detailed below.

A dose to treat human patients may range from about 1 mg to about 1000 mg of Formula I compound. The dose may be from about 1 mg, 2 mg, 2.5 mg, 4 mg, 5 mg, 7.5 mg, 10 mg, 12.5 mg, 15 mg, 17, 5 mg, 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg of a compound of Formula I-III, or any dose ranging between any two of those doses.

A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. A typical dose when administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating hyperproliferative diseases, conditions and/or disorders including, but not limited to, cancer. Accordingly, an aspect of this invention includes methods of treating, or preventing, diseases or conditions that can be treated or prevented by inhibiting Stat3. In one embodiment, the method comprises administering to a subject, in need thereof, a therapeutically effective amount of a compound of Formula I, or pharmaceutically acceptable salt thereof. In one embodiment, a human patient is treated with a compound of Formula I and a pharmaceutically acceptable carrier, adjuvant, or vehicle, wherein said compound of Formula I is present in an amount to treat cancer and/or detectably inhibit Stat3 activity.

Cancers which can be treated according to the methods of this invention include, but are not limited to, glioma, glioblastoma, neuroblastoma, breast, ovary, cervix, prostate, testis, genitourinary tract, esophagus, larynx, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Formula I compounds may be useful for in vitro, in situ, and in vivo diagnosis or treatment of mammalian cells, organisms, or associated pathological conditions, such as hyperproliferative disease and/or cancer.

Formula I compounds may be useful for treating conditions of the brain and central nervous system which require transport across the blood-brain barrier. Certain Formula I compounds have favorable penetrant properties for delivery to the brain. Disorders of the brain which may be effectively treated with Formula I compounds include metastatic and primary brain tumors, such as glioblastoma and melanoma.

Formula I compounds may be useful for treating eye cancers by localized delivery to the eye. Certain Formula I compounds have favorable properties for delivery to, and uptake into, the eye. Certain Formula I compounds may enhance efficacy and extend duration of response for treatment of wet AMD in combination with ranibizumab (LUCENTIS®, Genentech, Inc.) and bevacizumab (AVASTIN®, Genentech, Inc.).

Another aspect of this invention provides a compound of this invention for use in the treatment of the diseases or conditions described herein in a subject, e.g., a human, suffering from such disease or condition. Also provided is the use of a compound of this invention in the preparation of a medicament for the treatment of the diseases and conditions described herein in a warm-blooded animal, such as a mammal, e.g. a human, suffering from such disorder.

Pharmaceutical Formulation/Compositions and Uses

In order to use a Formula I compound for the therapeutic treatment (including prophylactic treatment) of mammals including humans, it is normally formulated in accordance with standard pharmaceutical practice as a pharmaceutical composition. According to this aspect of the invention, there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution (e.g. in saline).

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In addition to the compounds and salt forms provided herein, the invention includes pharmaceutical compositions, including tablets, capsules, solutions, and suspensions for parenteral and oral delivery forms and formulations, comprising a pharmaceutically acceptable carrier and therapeutically effective amounts of one or more of the Stat3 inhibitors herein provided. Stat3 inhibitor pharmaceutical compositions can include salts and hydrates.

In human and animal therapy for the treatment of cancer, for example in the treatment of cancer and other related disorders, diseases and conditions noted herein, the compounds and their crystal forms described and provided herein, their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing pharmaceutically acceptable excipients, such as starch or lactose, or in capsules or ovules either alone or in admixture with excipients, or in the form of elixirs, solutions or suspensions containing flavouring or colouring agents. They can also be injected parenterally, for example, intravenously, intramuscularly or subcutaneously. For parenteral administration, they are best used in the form of a sterile aqueous solution which may contain other substances, for example enough salts or monosaccharides to make the solution isotonic with blood. For buccal or sublingual administration they may be administered in the form of tablets or lozenges which can be formulated in a conventional manner.

As a general proposition, the initial pharmaceutically effective amount of the Formula I compound administered parenterally per dose will be in the range of about 0.01-10 mg/kg, 0.01-1.0, or 1.0 to 10.0 or 10.0 to 100.0 mg/kg. The amount of the Formula I compound administered parenterally per dose may also be about 0.05 to 5 mg/kg of patient body weight per day, with the typical initial range of compound used being 0.05 to 10 mg/kg/day. A typical dose may be about 1 mg to about 30.0 mg once, twice or four times a day of the compound. In some embodiments, the dose may be about 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, or about 4.0 mg/kg, or any range in between any two of the recited doses. In some embodiments the dose will be 0.08 mg/kg to about 0.5 mg/kg, from about 0.08 to about 0.24 mg/kg, or from about 0.24 to about 0.5 mg/kg. In another aspect, the effective dose of the STAT-3 inhibitor is given in one or more doses. For example, a therapeutically may be, for example, 0.08, 0.24, or 0.5 mg/kg for each dose.

Acceptable diluents, carriers, excipients and stabilizers are nontoxic to recipients at the dosages and concentrations employed, and include saline and/or buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, e.g., by coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (e.g., poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formulas I-III suitable for oral administration may be prepared as discrete units such as pills, capsules, cachets or tablets each containing a predetermined amount of a compound of Formula I-III.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, e.g., inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, e.g., 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I-III compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I-III may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 10 to 10,000 mg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, about 0.5 to 10% w/w, or about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, e.g. cocoa butter or a salicylate.

Formulations suitable for intrapulmonary or nasal administration have a particle size e.g. in the range of 0.1 to 500 microns (including particle sizes in a range between 0.1 and 500 microns in increments microns such as 0.5, 1, 30 microns, 35 microns, etc.) which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, e.g. sealed ampoules and vials, and may be stored in a freeze-dried (lyophilized) condition requiring only the addition of the sterile liquid carrier, e.g., water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone, or in combination with other therapeutic agents, for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result, e.g., from the condensation, oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., 14C or 3H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture/Kits

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The container may hold a compound of Formula I or a formulation thereof which is effective for treating the condition and may have a sterile access port (e.g., the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I-III, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, e.g. in the form of numbers, letters, or other markings or with a calendar insert, designating the days in the treatment schedule in which the dosages can be administered.

According to one embodiment, a kit may comprise (a) a first container with a compound of Formula I-III contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The invention includes an article of manufacture comprising packaging material containing one or more dosage forms containing a Stat3 inhibitors provided herein, wherein the packaging material has a label that indicates that the dosage form can be used for a subject having or suspected of having or predisposed to any of the diseases, disorders and/or conditions described or referenced herein. Such dosage forms include, for example, tablets, capsules, solutions and suspensions for parenteral and oral delivery forms and formulations.

In yet another aspect of this invention is a kit comprising (a) at least one Stat3 inhibitor, or salt or crystal thereof, and a pharmaceutically acceptable carrier, excipient and/or additive in a unit dosage form, and (b) means for containing the unit form. Since the present invention has an aspect that relates to the treatment of the disease/conditions described herein with a combination of active ingredients, the invention also relates to combining separate pharmaceutical compositions in kit form. A kit may contain a pharmaceucial composition comprising a Stat3 inhibitor, or salt or crystal thereof, as provided herein, either alone or together with a second compound as described herein.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Synthesis of Stat3 Inhibitors

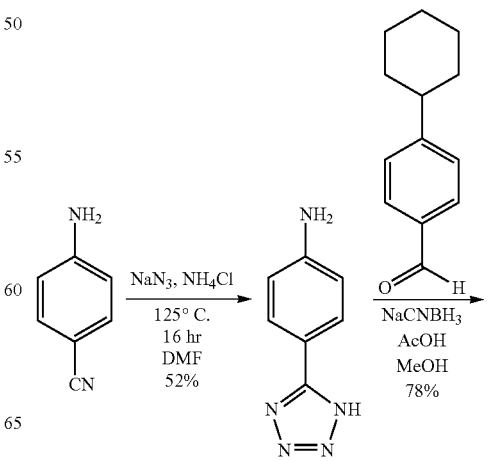

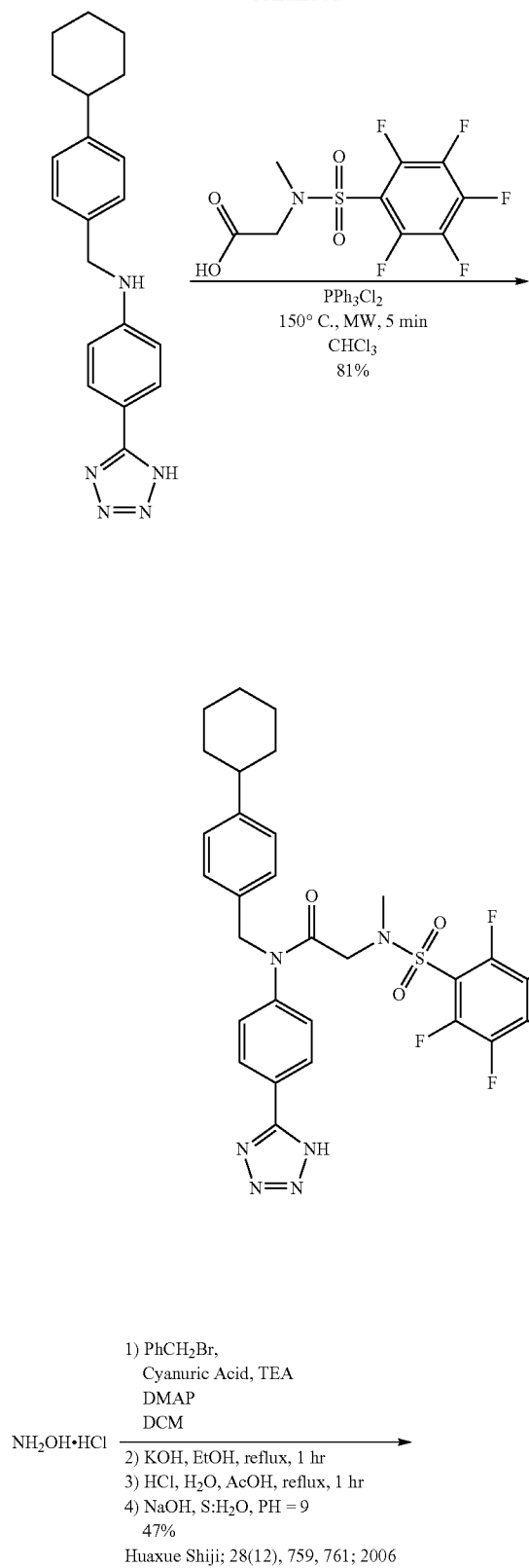
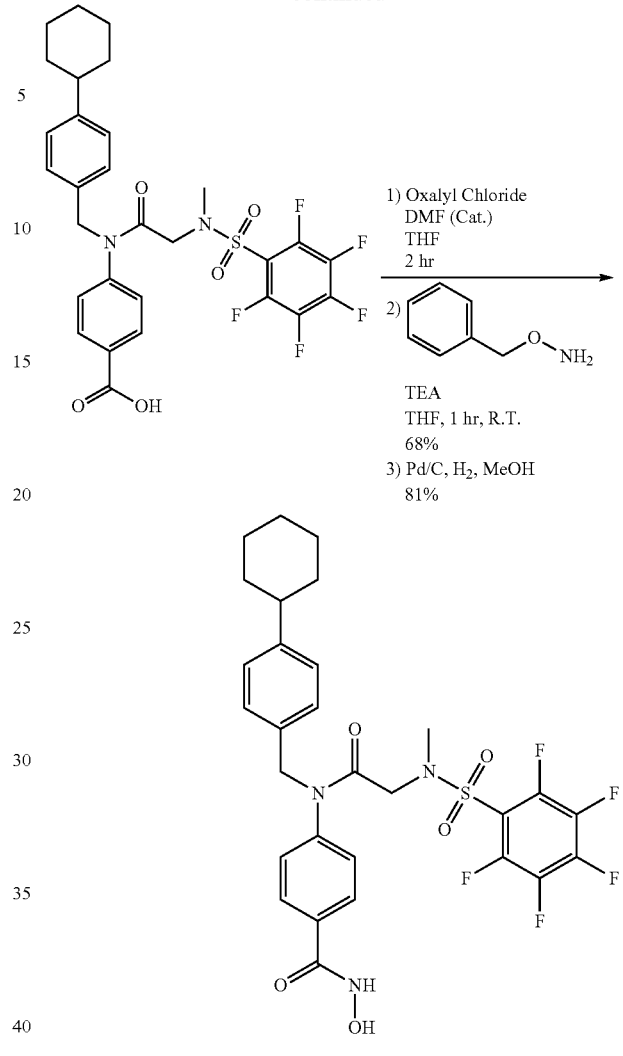
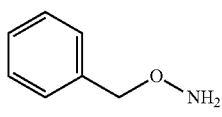

The reaction scheme shows a summary of an exemplary reaction scheme for the preparation of a Stat3 inhibitor of this invention, which may include a Stat3 inhibitor salt.

Organic acids include both aliphatic and aromatic carboxylic acids and include, for example, aliphatic monocarboxylic acids, aliphatic dicarboxylic acids, aliphatic tricarboxylic acids, aromatic monocarboxylic acids, aromatic dicarboxylic acids, aromatic tricarboxylic acids and other organic acids known to those of skill in the art.

Aliphatic carboxylic acids may be saturated or unsaturated. Suitable aliphatic carboxylic acids include those having from 2 to about 10 carbon atoms.

Aliphatic monocarboxylic acids include saturated aliphatic monocarboxylic acids and unsaturated aliphatic monocarboxylic acids. Examples of saturated monocarboxylic acids include acetic acid, propronic acid, butyric acid, valeric acid, caproic acid, enanthic acid, caprylic acid, pelargonic acid, and caprynic acid. Examples of unsaturated aliphatic monocarboxylic acids include acrylic acid, propiolic acid, methacrylic acid, crotonic acid and isocrotonic acid.

Aliphatic dicarboxylic acids include saturated aliphatic dicarboxylic acids and unsaturated aliphatic dicarboxylic acids. Examples of saturated aliphatic dicarboxylic acids include oxalic acid, malonic acid, succinic acid, glutaric acid, adipic acid, pimelic acid, suberic acid, azelaic acid, and sebacic acid. Examples of unsaturated aliphatic dicarboxylic acids include maleic acid, fumaric acid, citraconic acid, mesaconic acid, itaconic acid and the like.

In certain aspects, crystalline Stat3 inhibitors and salts thereof are described. These include crystalline Stat3 inhibitor maleate, Stat3 inhibitor fumarate, and Stat3 inhibitor succinate. Different Stat3 inhibitor crystals include those comprising the geometric structures, unit cell structures, and structural coordinates.

Also described are Stat3 inhibitor salts of high purity, methods for their preparation, and dosage forms including Stat3 inhibitor salts.

The pharmaceutical compositions may include, for example, one or more pharmaceutically acceptable excipients, carriers, and/or additives suitable for oral or parenteral administration.

The product formed by the described processes is substantially pure, that is, substantially free from any other compounds. Preferably, it contains less than 10% impurities, and more preferably, less than about 5% impurities, and even more preferably, less than about 1% impurities. The product thus formed is also preferably substantially pure, i.e., contains less than 10% impurity, more preferably less than 5% impurity, and still more preferably less than 1% impurity. The present invention also includes a substantially pure anhydrous crystalline form of Stat3 inhibitor disuccinate. The term "substantially pure" means that a sample of the relevant anhydrous crystalline form of Stat3 inhibitor disuccinate contains more than 90% of a single polymorphic form, preferably more than 95% of a single polymorphic form, and still more preferably more than 99% of a single polymorphic form.

Doses

In some embodiments, a therapeutically effective amount of the compounds herein and their pharmaceutically acceptable salts and solvates, may be from about 1 mg to about 1000 mg of Formula I compound. The dose may be from about 1 mg, 2 mg, 2.5 mg, 4 mg, 5 mg, 7.5 mg, 10 mg, 12.5 mg, 15 mg, 17, 5 mg, 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg of a compound of Formula I-III, or any dose ranging between any two of those doses.

In some embodiments, a typical dose may be about 1 mg to about 30.0 mg once, twice or four times a day of the compound. In some embodiments, the dose may be about 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, 4.0, 5.0, 6.0, 7.0, 8.0, 9.0, 10.0, 11.0, 12.0, 13.0, 14.0, 15.0, 16.0, 17.0, 18.0, 19.0, 20.0, 22.5, 25.0, 27.5, 30.0, 32.5, 35.0, 37.5, or about 40.0 mg/kg, or any range in between any two of the recited doses. In some embodiments the dose will be 0.08 mg/kg to about 0.5 mg/kg, from about 0.08 to about 0.24 mg/kg, or from about 0.24 to about 0.5 mg/kg. In another aspect, the effective dose of the STAT-3 inhibitor is given in one or more doses. For example, a therapeutically may be, for example, 0.08, 0.24, or 0.5 mg/kg for each dose.

A daily dosage level of the compounds herein, and their pharmaceutically acceptable salts and solvates, may be from about 1 mg to about 5 g per day, or up to about 50 g per day (in single or divided doses). Other therapeutically effective dose ranges include, for example, from about 5 mg to about 25 mg, from about 5 mg to about 15 mg, from about 4 mg to about 35 mg, from about 35 mg to about 50 mg, from about 50 mg to about 100 mg, from about 100 mg to about 200 mg, from about 200 mg to about 500 mg, or from about 500 mg to about 1000 mg per day.

Compounds described herein, and their pharmaceutically acceptable salts and solvates, will also be effective at doses in the order of 1/10, 1/50, 1/100, 1/200, 1/300, 1/400, 1/500 and even 1/1000 of those described herein.

In some embodiments of the invention, a therapeutically effective amount is the amount effective to elicit a plasma concentration of the compounds provided herein, and their pharmaceutically acceptable salts and solvates, from about 0.01 mg/L to about 20 mg/L, about 0.01 mg/L to about 15 mg/L, about 0.1 mg/L to about 10 mg/L, about 0.5 mg/L to about 9 mg/L, about 1 mg/L to about 8 mg/L, about 2 mg/L to about 7 mg/L or about 3 mg/L to about 6 mg/L.

The doses described herein, may be administered in a single dose or multiple doses. For example, doses may be administered once, twice, three, four or more times a day, or one, two, three, four, five, or six times per week.

The physician will determine the actual dosage which will be most suitable for an individual patient, and it will vary with the age, weight and response of the particular patient. The above dosages are exemplary of the average case; there can, of course, be individual instances where higher or lower dosage ranges are merited, and such are within the scope of this invention.

Generally, in humans, IP administration of the compounds of the invention is the preferred route. A preferred oral dosing regimen in cancer treatment for a typical man is from about 1 mg to about 1000 mg per day of compound when required. Preventative doses are lower, typically from about 0.3-100 mg to about 1-50 mg per day.

For veterinary use, a compound provided herein, or a veterinarily acceptable salt thereof, or a veterinarily acceptable solvate of either entity, is administered as a suitably acceptable formulation.

Thus the invention provides a pharmaceutical composition comprising a Stat3 inhibitor a summary of an exemplary reaction scheme for the preparation of Stat3 inhibitor, which may include a Stat3 inhibitor salt compound provided herein, or a pharmaceutically acceptable salt thereof, or a pharmaceutically acceptable solvate of either entity, together with a pharmaceutically acceptable diluent or carrier.

It further provides a veterinary formulation comprising a Stat3 inhibitor provided herein, or a veterinarily acceptable salt thereof, or a veterinarily acceptable solvate of either entity, together with a veterinarily acceptable diluent or carrier.

The invention also provides a Stat3 inhibitor provided herein, or a pharmaceutically acceptable salt thereof, or a pharmaceutically acceptable solvate of either entity, or a pharmaceutical composition containing any of the foregoing, for use as a human medicament.

In addition, it provides a Stat3 inhibitor compound provided herein, or a veterinarily acceptable salt thereof, or a veterinarily acceptable solvate of either entity, or a veterinary formulation containing any of the foregoing, for use as an animal medicament.

In yet another aspect, the invention provides the use of a Stat3 inhibitor provided herein, or a pharmaceutically acceptable salt thereof, or a pharmaceutically acceptable solvate of either entity, for the manufacture of a human medicament for the curative or prophylactic treatment of a medical condition for which a Stat3 inhibitor is indicated.

It also provides the use of a Stat3 inhibitor compound provided herein, or a veterinarily acceptable salt thereof, or a veterinarily acceptable solvate of either entity, for the manufacture of an animal medicament for the curative or prophylactic treatment of a medical condition for which a Stat3 inhibitor is indicated.

Moreover, the invention includes use of the compounds and compositions provided herein for methods for treating and/or preventing, in whole or in part, various diseases, disorders and conditions, including but not limited to hyperproliferative disease such as cancer.

The invention also includes pharmaceutical compositions, including tablets and capsules and other oral delivery forms and formulations, comprising a pharmaceutically acceptable carrier and therapeutically effective amounts of a Stat3 inhibitor as provided herein.

The invention includes methods for the use of therapeutically effective amounts of a Stat3 inhibitor provided herein in the manufacture of a medicament. Such medicaments include, for example, tablets, capsules, solutions and suspensions for parenteral and oral delivery forms and formulations. Such medicaments include those for the treatment of a subject as disclosed herein.

The compounds of the invention, particularly Stat3 inhibitor salts, and hydrates, for example, in the disclosed crystal form, may also be prepared with another anti-cancer agent.

Doses for such Stat3 inhibitors, salts and/or solvates as provided herein are envisaged to be administered in a therapeutically effective amount, for example, to inhibit cancer, delay tumor progression, and/or ro reduce multidrug resistance in a subject.

The invention includes a formulation comprising a Stat3 inhibitor provided herein in amounts effective to reduce glutathione transport in the body of a subject. Such formulations include, for example, tablets, capsules, solutions and suspensions for parenteral and oral delivery forms and formulations.

Methods of Administration of Stat3 Inhibitors

The present invention is based a surprising, and unexpected, discovery that the Stat3 inhibitors of this invention are potent, selective inhibitors of Stat3 with anti-tumor activity. In addition, aspects of the present invention are based on the surprising discovery that the potent and selective Stat3 inhibitors of this invention have the ability to treat cancer, for example, to suppress, and/or prevent metastasis of cancer cells.

For the purpose of the current disclosure, the following definitions shall, in their entireties, be used to define technical terms, and to define the scope of the composition of matter for which protection is sought in the claims.

The instant disclosure provides methods of treatment by administration to a subject of one or more effective dose(s) of Stat3 inhibitors for a duration to achieve the desired therapeutic effect. The subject is preferably a mammal, including, but not limited to, animals such as cows, pigs, horses, chickens, cats, dogs, etc., and is most preferably human.

Various delivery systems are known, and can be used to administer a Stat3 inhibitor in accordance with the methods of the invention, e.g., encapsulation in liposomes, microparticles or microcapsules. Methods of introduction include, but are not limited to, topical, subcutaneous, intradermal, intramuscular, intraperitoneal, intravenous, subcutaneous, intranasal, epidural, and oral routes. For treatment of certain cancers, topical, subcutaneous, intradermal, and systemic deliveries can be particularly efficacious.

Stat3 inhibitors can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce pharmaceutical compositions comprising a Stat3 inhibitor into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. It may be desirable to administer the pharmaceutical compositions comprising Stat3 inhibitor locally to the area in need of treatment; this may be achieved, for example, and not by way of limitation, by topical application, by injection, by means of a catheter, by means of a suppository, or by means of an implant, said implant being of a porous, non-porous, or gelatinous material, including membranes, such as Silastic™ membranes, or fibers.

Still other modes of administration of Stat3 inhibitors involve delivery in a controlled release system. In certain embodiments, a pump may be used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)). Additionally polymeric materials can be used (see Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983; see also Levy et al., Science 228:190 (1985); During et al., Ann. Neurol. 25:351 (1989); Howard et al., J. Neurosurg. 71:105 (1989)), or a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Forms and Dosages of Compositions Comprising STAT-3 Inhibitors

As used herein, for cancer treatment, lyophilized formulation and liquid formulation suitable for injection are particularly efficacious. Suitable dosage forms of Stat3 inhibitors for use in embodiments of the present invention encompass physiologically/pharmaceutically acceptable carriers that are inherently non-toxic and non-therapeutic. Examples of such carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, P6N (Neumedicines, Pasadena, Ca.) and PEG. Carriers for topical or gel-based forms of Stat3 inhibitors include polysaccharides, such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and .gamma ethyl-L-glutamate (Sidman et al, supra), non-degradable ethylene-vinyl acetate (Langer et al., supra), degradable lactic acid-glycolic acid copolymers such as the Lupron Depot™ (injectable microspheres composed of lactic acid-glycolicacid copolymer and leuprolide acetate), and poly-D-(–)-3-hydroxybutyric acid. While polymers, such as ethylene-vinyl acetate and lactic acid-glycolic acid, enable release of molecules for over 100 days, certain hydrogels release proteins for shorter time periods. When encapsulated Stat3 inhibitors remain in the body for a long time, they may denature, or aggregate, as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In the case of administrations over several days or longer, depending on the condition, the treatment is sustained until a desired suppression of disease symptoms occurs. However, other dosage regimens may be useful. The progress of this therapy is easily monitored by conventional techniques and assays.

Therapeutic formulations comprising Stat3 inhibitors are prepared for storage by mixing Stat3 inhibitors, having the desired degree of purity, with optional physiologically acceptable carriers, excipients, or stabilizers (Remington's Pharmaceutical Sciences, 16th edition, Osol, A., Ed., (1980)), in the form of lyophilized cake, or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween®, Pluronics™ or polyethylene glycol (PEG).

The term "buffer", as used herein, denotes a pharmaceutically acceptable excipient, which stabilizes the pH of a pharmaceutical preparation. Suitable buffers are well known in the art and can be found in the literature. Pharmaceutically acceptable buffers include, but are not limited to, histidine-buffers, citrate-buffers, succinate-buffers, acetate-buffers, phosphate-buffers, arginine-buffers, or mixtures thereof. The abovementioned buffers are generally used in an amount of about 1 mM to about 100 mM, of about 5 mM to about 50 mM and of about 10-20 mM. The pH of the buffered solution can be at least 4.0, at least 4.5, at least 5.0, at least 5.5 or at least 6.0. The pH of the buffered solution can be less than 7.5, less than 7.0, or less than 6.5. The pH of the buffered solution can be about 4.0 to about 7.5, about 5.5 to about 7.5, about 5.0 to about 6.5, and about 5.5 to about 6.5 with an acid or a base known in the art, e.g. hydrochloric acid, acetic acid, phosphoric acid, sulfuric acid and citric acid, sodium hydroxide and potassium hydroxide. As used herein when describing pH, "about" means plus or minus 0.2 pH units.

As used herein, the term "surfactant" can include a pharmaceutically acceptable excipient which is used to protect protein formulations against mechanical stresses, like agitation and shearing. Examples of pharmaceutically acceptable surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulphate (SDS). Suitable surfactants include polyoxyethylenesorbitan-fatty acid esters such as polysorbate 20, (sold under the trademark Tween 20®) and polysorbate 80 (sold under the trademark Tween 80®). Suitable polyethylene-polypropylene copolymers are those sold under the names Pluronic® F68 or Poloxamer 188®. Suitable Polyoxyethylene alkyl ethers are those sold under the trademark Brij®. Suitable alkylphenolpolyoxyethylene esthers are sold under the tradename Triton-X. When polysorbate 20 (Tween 20®) and polysorbate 80 (Tween 80®) are used, they are generally used in a concentration range of about 0.001 to about 1%, of about 0.005 to about 0.2% and of about 0.01% to about 0.1% w/v (weight/volume).

As used herein, the term "stabilizer" can include a pharmaceutically acceptable excipient, which protects the active pharmaceutical ingredient and/or the formulation from chemical and/or physical degradation during manufacturing, storage and application. Chemical and physical degradation pathways of protein pharmaceuticals are reviewed by Cleland et al., Crit. Rev. Ther. Drug Carrier Syst., 70(4):307-77 (1993); Wang, Int. J. Pharm., 7S5(2): 129-88 (1999); Wang, Int. J. Pharm., 203(1-2): 1-60 (2000); and Chi et al, Pharm. Res., 20(9): 1325-36 (2003). Stabilizers include, but are not limited to, sugars, amino acids, polyols, cyclodextrines, e.g. hydroxypropyl-beta-cyclodextrine, sulfobutylethyl-beta-cyclodextrin, beta-cyclodextrin, polyethylenglycols, e.g. PEG 3000, PEG 3350, PEG 4000, PEG 6000, albumine, human serum albumin (HSA), bovine serum albumin (BSA), salts, e.g., sodium chloride, magnesium chloride, calcium chloride, chelators, e.g., EDTA as hereafter defined. As mentioned hereinabove, stabilizers can be present in the formulation in an amount of about 10 to about 500 mM, an amount of about 10 to about 300 mM, or in an amount of about 100 mM to about 300 mM. In some embodiments, exemplary STAT-3 inhibitors can be dissolved in an appropriate pharmaceutical formulation, wherein it is stable.

Stat3 inhibitors also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

Stat3 inhibitors to be used for in vivo administration must be sterile. This is readily accomplished by filtration through sterile filtration membranes, prior to, or following, lyophilization and reconstitution. Stat3 inhibitors ordinarily will be stored in lyophilized form, or in solution. Therapeutic Stat3 inhibitors compositions generally are placed into a container having a sterile access port, for example, an intravenous solution bag, or vial, having a stopper pierceable by a hypodermic injection needle.

When applied topically, Stat3 inhibitors is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with, or without, purified collagen. The compositions also may be impregnated into transdermal patches, plasters, and bandages, preferably in liquid or semi-liquid form.

For obtaining a gel formulation, Stat3 inhibitors formulated in a liquid composition may be mixed with an effective amount of a water-soluble polysaccharide, or synthetic polymer, such as PEG, to form a gel of the proper viscosity to be applied topically. The polysaccharide that may be used includes, for example, cellulose derivatives, such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the Stat3 inhibitor molecule held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose, when mixed in the proper ratio to obtain a paste.

The term "water soluble", as applied to the polysaccharides and PEGs, is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and the Stat3 inhibitor is present in an amount of about 5-100 mg per ml of gel or up to about 0.5 mM in 0.5% DMSO (in PBS or H20) based on the limit of solubility.

An effective amount of Stat3 inhibitors to be employed therapeutically will depend, for example, upon the therapeutic objectives, the route of administration, and the condition of the patient. Accordingly, it will be necessary for the therapist to titer the dosage and modify the route of administration, as required to obtain the optimal therapeutic effect. Typically, the clinician will administer Stat3 inhibitors until a dosage is reached that achieves the desired effect. In certain embodiments, the appropriate dosing can be determined based on an amount of Stat3inhibitors administered per surface area of the affected region.

"Near the time of administration of the treatment" refers to the administration of Stat3 inhibitors at any reasonable time period, either before, and/or after the administration of the treatment, such as about one month, about three weeks, about two weeks, about one week, several days, about 120 hours, about 96 hours, about 72 hours, about 48 hours, about 24 hours, about 20 hours, several hours, about one hour or minutes. Near the time of administration of the treatment may also refer to either the simultaneous, or near simultaneous, administration of the treatment and Stat3 inhibitors, i.e., within minutes to one day.

"Chemotherapy" refers to any therapy that includes natural or synthetic agents now known, or to be developed in the medical arts. Examples of chemotherapy include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include combined chemotherapy with docetaxel, cisplatin, and 5-fluorouracil, for patients with locally advanced squamous cell carcinoma of the head (Tsukuda, M. et al., Int J Clin Oncol. 2004 June; 9 (3): 161-6), and fludarabine and bendamustine in refractory and relapsed indolent lymphoma (Konigsmann M, et al., Leuk Lymphoma. 2004; 45 (9): 1821-1827).

As used herein, exemplary sources of therapeutic or accidental ionizing radiation can include, for example, alpha, beta, gamma, x-ray, and neutron sources.

"Radiation therapy" refers to any therapy where any form of radiation is used to treat the disease state. The instruments that produce the radiation for the radiation therapy are either those instruments currently available, or to be available in the future.

"Chemoprotection or radioprotection" refers to protection from, or an apparent decrease in, the associated hematopoietic toxicity of a treatment intended to target the disease state.

"Solid tumors" generally refers to the presence of cancer of body tissues other than blood, bone marrow, or the lymphatic system.

EXAMPLES

The invention is now described with reference to the following Examples. These Examples are provided for the purpose of illustration only, and the invention is not limited to these Examples, but rather encompasses all variations that are evident as a result of the teaching provided herein.

The Examples below demonstrate that the potent and selective STAT-3 inhibitors of Formulas 1-III have efficacy for treating cancer and other proliferative diseases. Aspects and embodiments of the instant disclosure stem from the unexpected discovery that certain STAT-3 inhibitor formulations have surprising, and unexpected, utility and efficacy when administered to a subject.

The therapeutically effective STAT-3 inhibitors of this invention can be prepared according to the synthetic scheme outlined above. However, the invention is not limited to that method. The compositions may also be prepared as described for structurally related compounds in the literature.

Example 1: Selective Inhibition of Stat3 DNA-Binding Activity by SH5-07 and SH4-54

Characterization of SH5-07 and SH4-54 for use as an orally-bioavailable Stat3 inhibitors in vitro and in vivo is hereby described, including the ability to inhibit growth of mouse xenografts of human breast and non-small cell lung cancers.

Nuclear magnetic resonance (NMR) structural analysis supports biophysical studies of the interaction of agents with Stat3 and more notably reveals that SH4-54 interacts with Stat3 at three sites within both the SH2 and DNA-binding domains, suggesting another binding site in the Stat3 protein that was previously unknown. In model human glioma, U251MG and U373MG, breast cancer, MDA-MB-231, non-small-cell lung cancer, A549, and prostate cancer, DU145 cell lines harboring aberrantly-active Stat3, SH5-07 or SH-4-54 inhibited constitutive Stat3 phosphorylation, DNA-binding or transcriptional activities at low concentrations of 1-10 µM in a time-dependent manner.

By contrast, both agents had little or no effect on Stat1 or Stat5 DNA-binding activity, or on pSrc, pJanus kinase (JAK)2, pShc, pAkt, and pERK1/2MAPK (extracellular signal regulated kinase/mitogen activated protein kinase) levels, or on Stat3-independent transcriptional events. Further, SH5-07 or SH-4-54 selectively suppressed cell viability and growth, and induced cell cycle arrest and apoptosis, and inhibited the migration in vitro of human breast cancer and glioma cells that harbor aberrant Stat3 activity. Treatment of human glioma or breast cancer cells with SH5-07 or SH4-54 down-regulated the expression of known Stat3-regulated genes, including Bcl-2, Bcl-xL, Cyclin D1, c-Myc and Survivin. Oral gavage administration of SH5-07 inhibits growth of human glioma xenografts. The studies described herein identify SH5-07 and SH4-54 as potent and selective Stat3 inhibitors that induce antitumor cell effects in vitro and antitumor effects in vivo.

Selective Inhibition of Stat3 DNA-Binding Activity by SH5-07 and SH4-54.

Nuclear extracts containing activated Stat3 prepared from v-Src-transformed mouse fibroblasts (NIH3T3/v-Src) were pre-incubated with increasing concentration of SH5-07 or SH4-54 for 30 min at room temperature, prior to incubation with the radiolabeled high affinity sis-inducible element (hSIE) probe that binds to Stat3 and Stat1 and subjecting to electrophoretic mobility shift assay (EMSA) analysis, as always done. See Siddiquee et al., Selective chemical probe inhibitor of Stat3, identified through structure-based virtual screening, induces antitumor activity. Proc Natl Acad Sci USA. 104:7391-7396 (2007); Siddiquee et al., An Oxazole-Based Small-Molecule Stat3 Inhibitor Modulates Stat3 Stability and Processing and Induces Antitumor Cell Effects. ACS Chem. Biol. 2:787-798 (2007); Zhang et al., Orally bioavailable small-molecule inhibitor of transcription factor Stat3 regresses human breast and lung cancer xenografts, Proc Natl Acad Sci USA 109:9623-8 (Jun. 12, 2012).

Cells and Reagents.

Normal mouse fibroblasts (NIH3T3) and counterparts transformed by v-Src (NIH3T3/v-Src), or overexpressing the human epidermal growth factor (EGF) receptor (NIH3T3/hEGFR), and the human breast cancer (MDA-MB-231) and pancreatic cancer (Panc-1) cells have all been previously reported. See Turkson et al., Phosphotyrosyl peptides block Stat3-mediated DNA-binding activity, gene regulation and cell transformation. J. Biol. Chem. 276: 45443-45455 (2001); Johnson et al., Overexpressed pp60c-src can induce focus formation without complete transformation of NIH 3T3 cells. Mol. Cell. Biol. 5:1073-1083 (1985); Yu et al., Enhanced DNA-binding activity of a Stat3-related protein in cells transformed by the Src oncoprotein. Science 269:81-83 (1995); Garcia et al., Constitutive activation of Stat3 by the Src and JAK tyrosine kinases participates in growth regulation of human breast carcinoma cells. Oncogene 20:2499-2513 (2001). The Stat3-dependent luciferase reporter, pLucTKS3 and the Stat3-independent counterpart driven by the serum response element (SRE) of the c-fos promoter (pLucSRE) have been previously reported (15, 33). Cells were grown in Dulbecco's modified Eagle's medium (DMEM) containing 10% heat-inactivated fetal bovine serum. Antibodies against Stat3, pY705Stat3, Src, pY416Src, Erk1/2, and pErk1/2 are from Cell Signaling Technology (Danvers, Mass.).

Nuclear Extract Preparation, Gel Shift Assays, and Densitometric Analysis.

Nuclear extract preparations and electrophoretic mobility shift assay (EMSA) were carried out as previously described. Yu et al., 1995; Turkson et al., Stat3 activation by Src induces specific gene regulation and is required for cell transformation. Mol. Cell. Biol. 18:2545-2552 (1998). The $^{32}$P-labeled oligonucleotide probes used were hSIE (high affinity sis-inducible element from the c-fos gene, m67 variant, 5'-AGCTTCATTTCCCGTAAATCCCTA) (SEQ ID NO: 1) that binds Stat1 and Stat3 and MGFe (mammary gland factor element from the bovine β-casein gene promoter, 5'-AGATTTCTAGGAATTCAA) (SEQ ID NO: 2) for Stat1 and Stat5 binding. Wagner et al., The SIF binding element confers sis/PDGF inducibility onto the c-fos promoter. EMBO J. 9:4477-4484 (1990); Gouilleux et al., Prolactin and interleukin-2 receptors in T lymphocytes signal through a MGF-STATS-like transcription factor. Endocrinology 136:5700-5708 (1995). Except where indicated, nuclear extracts were pre-incubated with compound for 30 min at room temperature prior to incubation with the radio-labeled probe for 30 min at 30° C. before subjecting to EMSA analysis. Bands corresponding to DNA-binding activities were scanned and quantified for each concentration of compound using ImageQuant and plotted as percent of control (vehicle) against concentration of compound, from which the $IC_{50}$ values were derived, as previously reported. Turkson et al., A novel platinum compound inhibits constitutive Stat3 signaling and induces cell cycle arrest and apoptosis of malignant cells. J Biol Chem. 280:32979-32988 (2005).

The results of the studies show that Stat3 DNA-binding activity was inhibited in a dose-dependent manner by both SH5-07 and SH4-54 (FIG. 1B(i) and (ii)), with average $IC_{50}$ values of 3.9±0.6 µM and 4.4±0.3 µM, respectively, which represents a 1.5 to 2-fold improvement over that of BP-1-102 ($IC_{50}$ of 6.8 µM). Zhang et al. (2012). By contrast, both compounds showed minimal effects on Stat1:Stat1 or Stat5:Stat5 DNA-binding activity (FIG. 1C) in a similar DNA-binding assay with EMSA analysis using nuclear extracts containing activated Stat1 and Stat5 prepared from EGF-stimulated NIH3T3/hEGFR (mouse fibroblasts over-expressing the human epidermal growth factor receptor, EGFR) and the mammary gland factor element (MGFe) probe, as previously done. Siddiquee et al., Selective chemical probe inhibitor of Stat3, identified through structure-based virtual screening, induces antitumor activity, Proc Natl Acad Sci USA. 104:7391-7396 (2007). Accordingly, these results further demonstrate that the compounds of this invention are potent and selective inhibitors of STAT-3.

Figure 4:
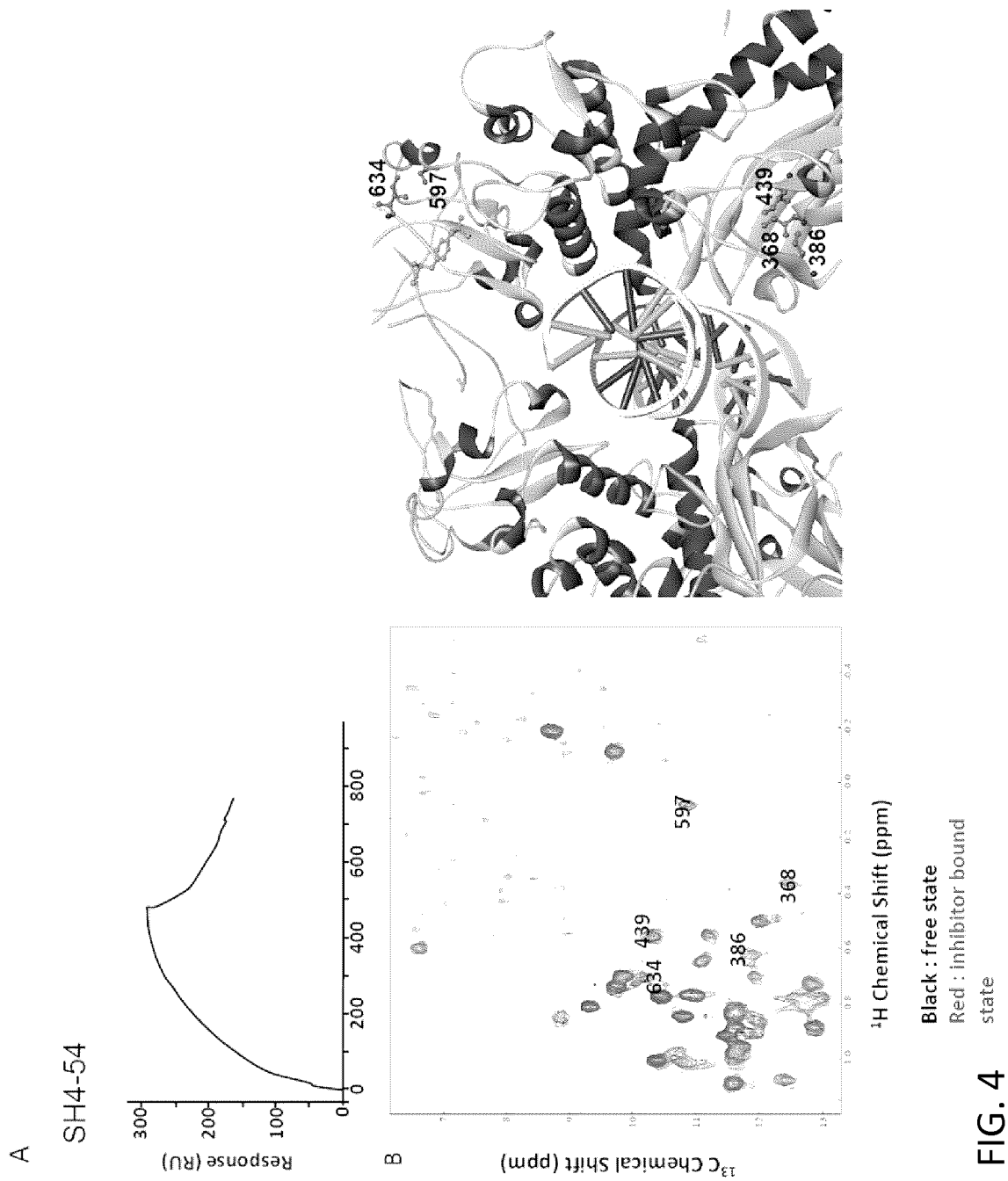
FIG. 4. SH4-54 interacts with Stat3. (A), Surface plasmon resonance analysis of the interaction of SH4-54 with purified Stat3 protein; and (B), Nuclear magnetic resonance (NMR) analysis of the interactions of Stat3 with SH4-54 in solution and the observed chemical shifts of isoleucine residues of the Stat3 protein. Data are representative of 2-3 independent determinations.

Surface plasmon resonance (SPR) analysis was also conducted to further study the effect of the STAT-3 inhibitors on Stat3. Results showed that SH4-54 bound to Stat3, with affinities ($K_D$) of 2.4 (FIG. 4A). Nuclear magnetic resonance (NMR) approach was further used to verify the binding of SH4-54 to Stat3. The 1D $^1$H NMR spectra of 200 µM SH4-54 in DMSO suggest an effective concentration of 20 µM in each case (Supplemental FIG. S1) due to precipitation. Comparison of the free and bound states of Stat3 with SH4-54 based on the $^1$H and $^{13}$C chemical shifts of isoleucine (Ile) residues show evidence of changes in the Stat3 SH2 and DNA-binding domains in Ile634 and Ile597, and Ile368, Ile386, Ile439 (FIG. 4B).

Example 2: Inhibition of Constitutive Stat3 Activation

Figure 2:
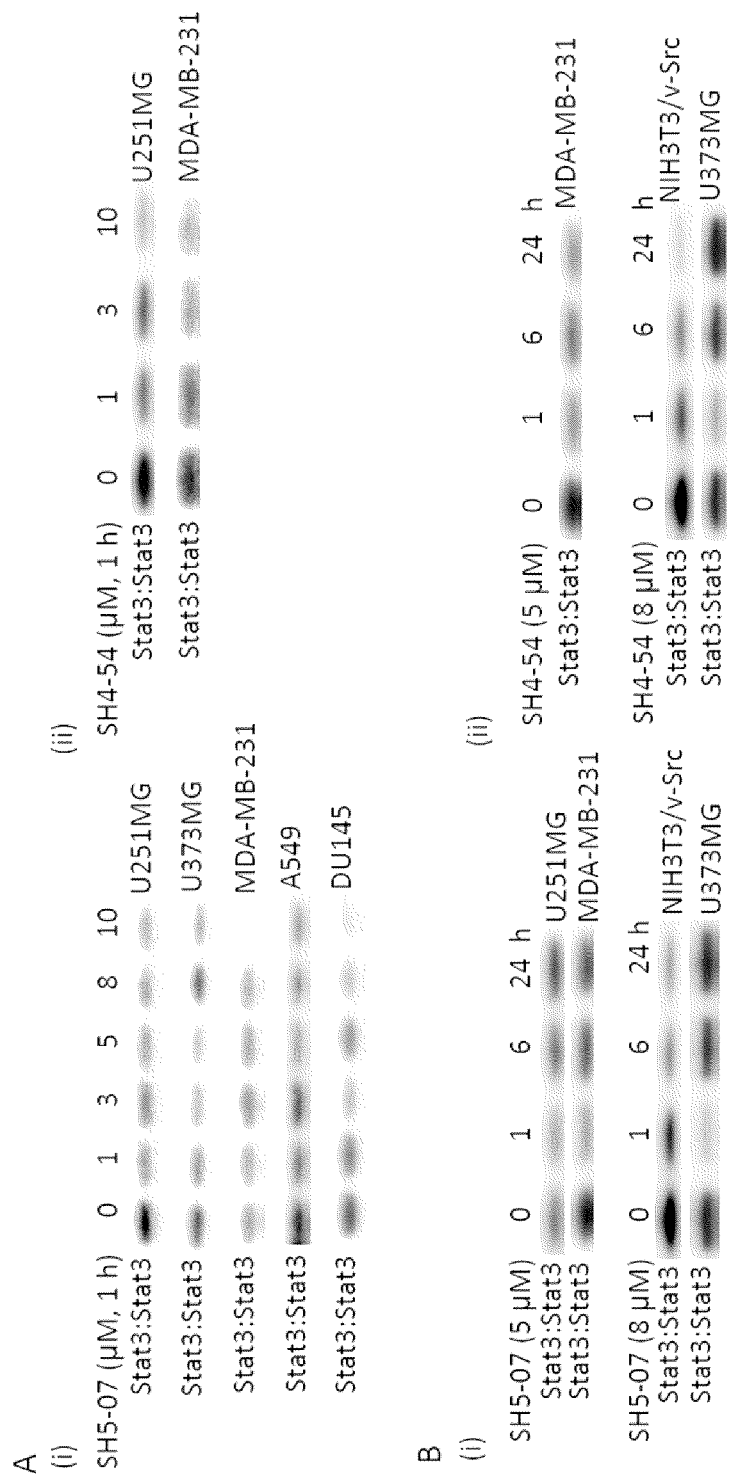
FIG. 2. Effects of SH5-07 and SH4-54 on Stat3 phosphorylation, DNA-binding and transcriptional activities and on Stat3-independent signal transduction. (A and B) Nuclear extracts of equal total protein prepared from malignant cells harboring constitutively-active Stat3 and treated for (A) 1 h with increasing concentrations of (i) SH5-07 or (ii) SH4-54 or (B) with 5 or 8 μM of (i) SH5-07 or (ii) SH4-54 for the indicated times were subjected to in vitro DNA-binding assay using the radiolabeled hSIE probe and analyzed by EMSA; (C, D and E) SDS-PAGE and Western blotting analysis of whole-cell lysates of equal total protein prepared from the indicated malignant cells harboring constitutively-active Stat3 and treated for (C) 1 h with increasing concentration of (i) SH5-07 or (ii) SH4-54, or (D) with 5 or 8 μM of (i) SH5-07 or SH4-54 for 0-24 h, or (E) with 5 μM SH5-07 for 0-9 h with a re-dosing at 5 h (5+1) and probing for pY705Stat3 or Stat3; (F) Normal NIH3T3 cells were transiently co-transfected with the plasmid encoding v-Src and the (i) Stat3-dependent luciferase reporter, pLucTKS3 or (ii) the Stat3-independent luciferase reporter, pLucSRE for 24 h and treated with 0-8 μM SH5-07 for an additional 24 h. Luciferase reporter activity was assayed in cytosolic extracts with a luminometer; and (G) SDS-PAGE and Western blotting analysis of whole-cell lysates of equal total protein prepared from the human breast cancer cell line (ductal carcinoma), MDA-MB-231 (i) and human glioma cell line U251MG (ii) cells treated for 1 h with 0-10 M SH5-07 and probing for pY1068EGFR, EGFR, pJAK2, JAK2, pSrc, Src, pERK$^{MAPK}$, ERK$^{MAPK}$, pAkt, Akt, and β-Actin. Positions of STATs:DNA complexes or proteins in gel are labeled; control lanes (0) represent nuclear extracts treated with 0.05% DMSO, or nuclear extracts or whole-cell lysates prepared from 0.05% DMSO-treated cells. Values shown in each panel are means plus standard deviations of at least four independent transfections, each performed in triplicate. For each transfection, luciferase activity was normalized to transfection efficiency, with β-Gal activity as an internal control. *-<0.05. Data are representative of 3-4 independent determinations.
Figure 2:
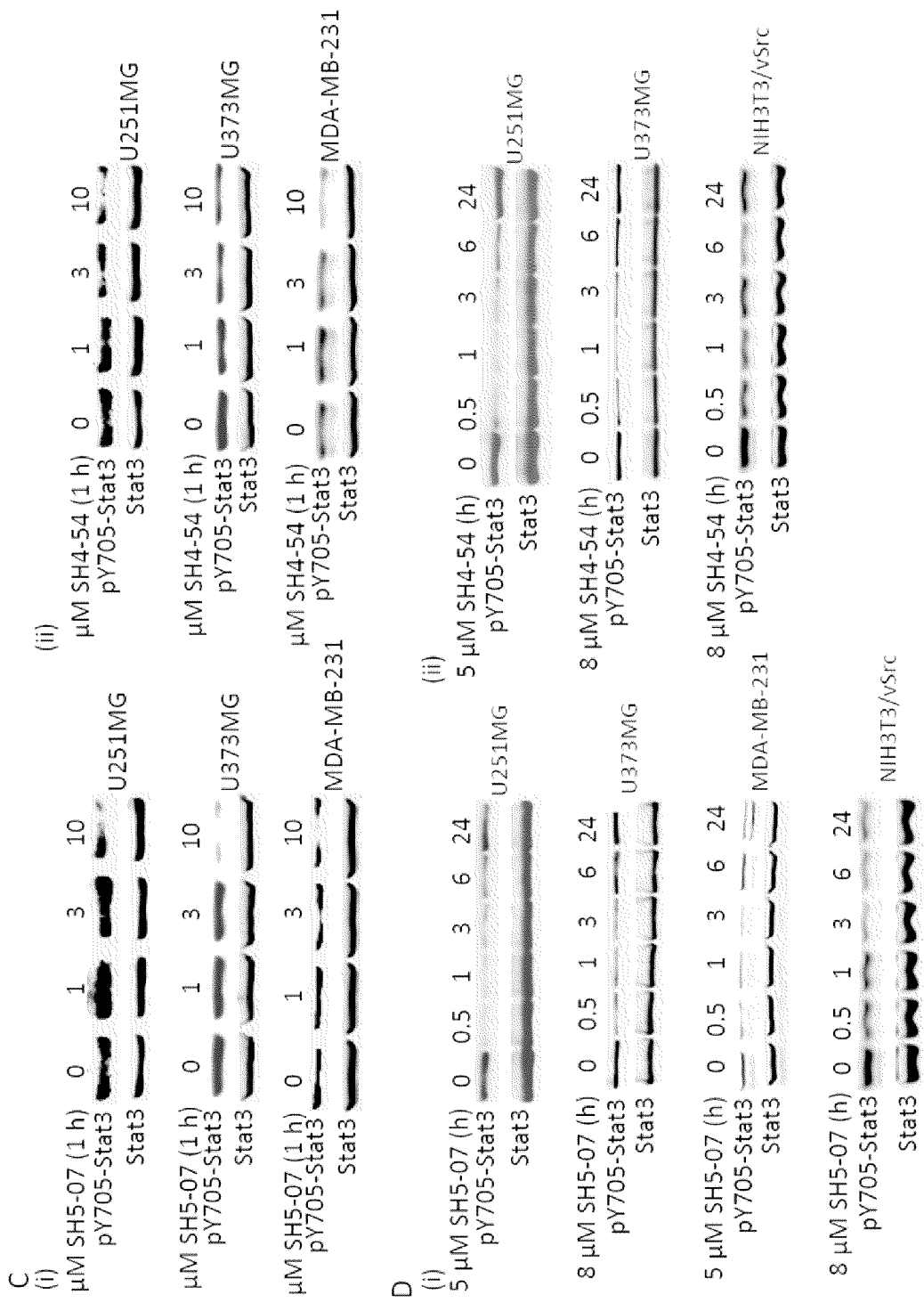
Figure 2:
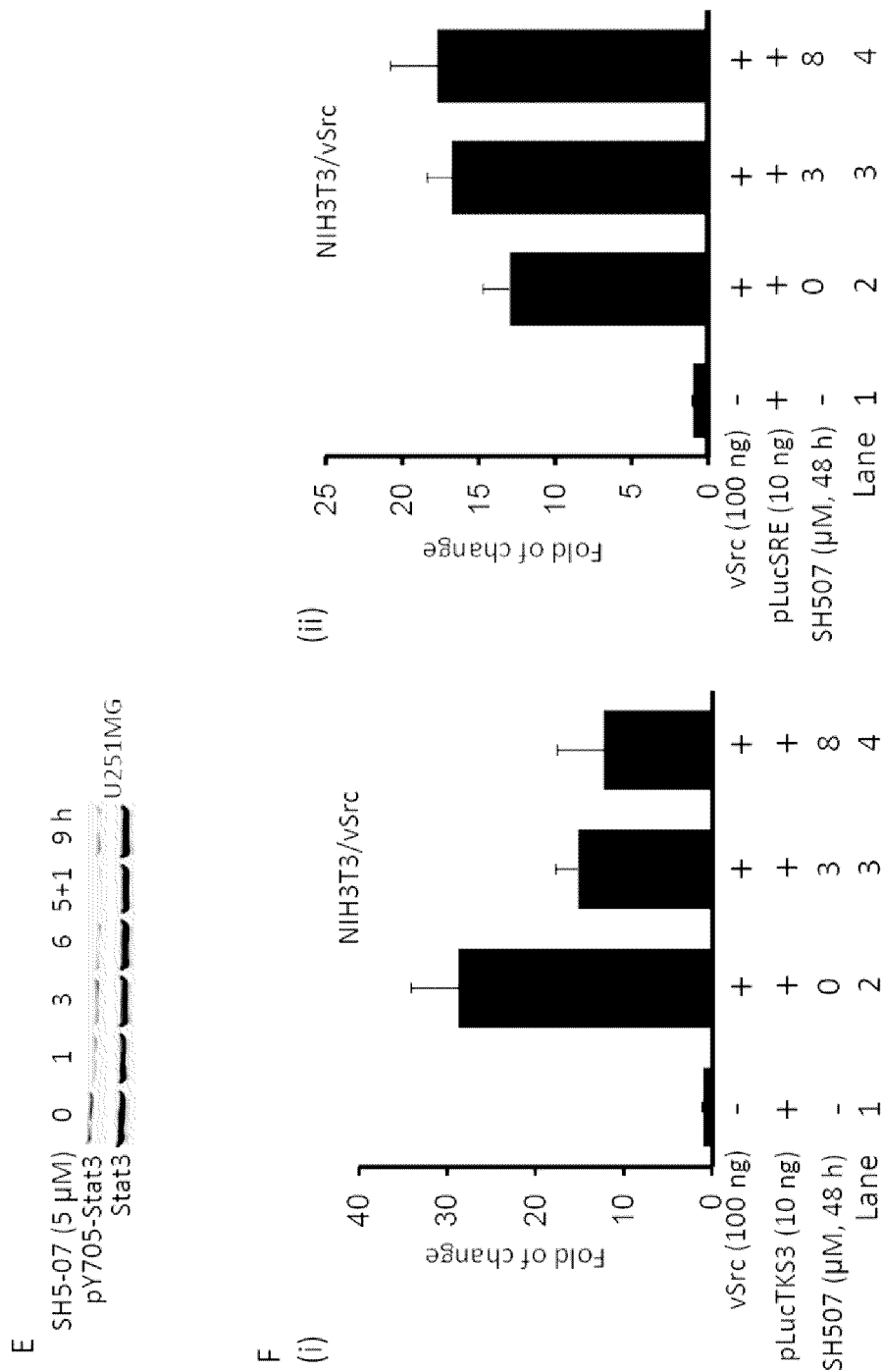
Figure 2:
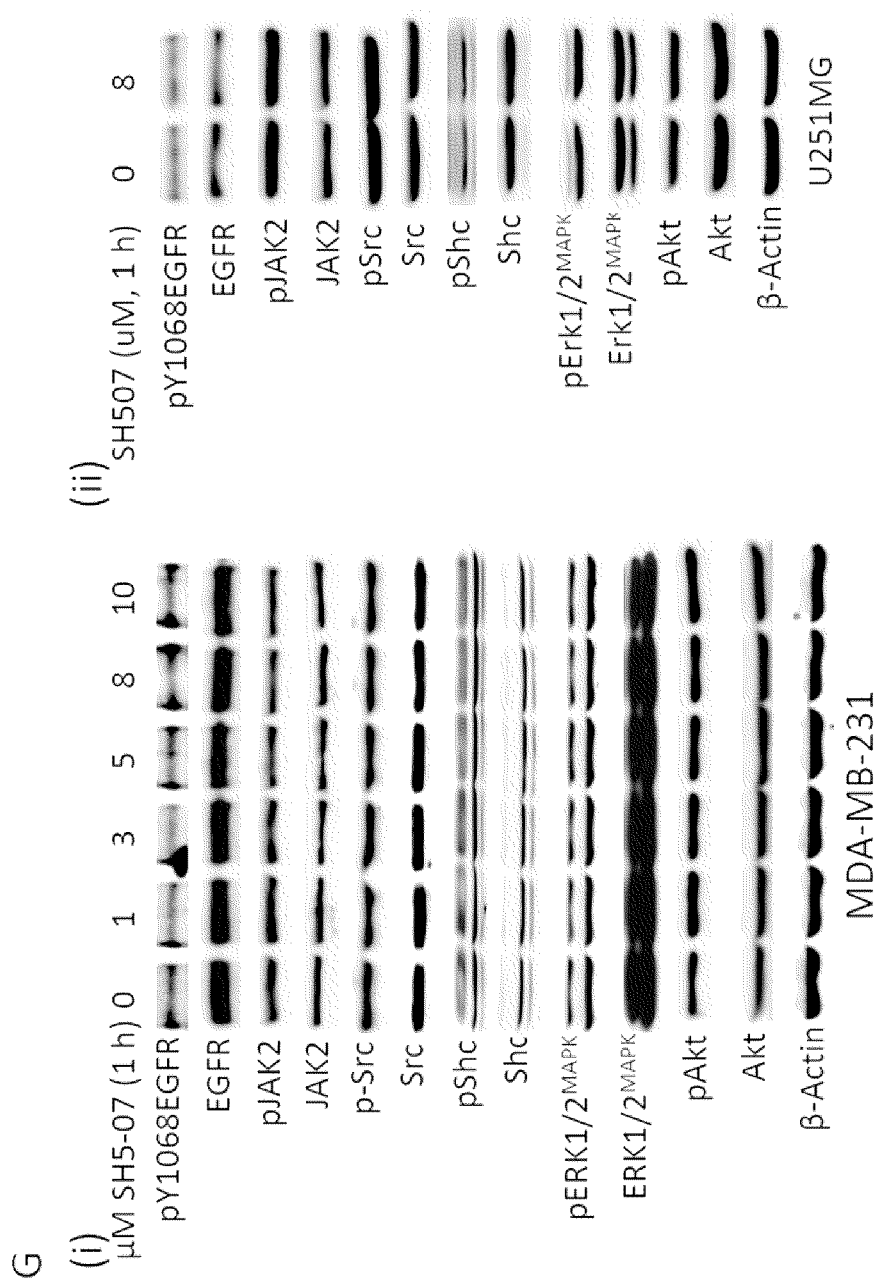
Figure 2:
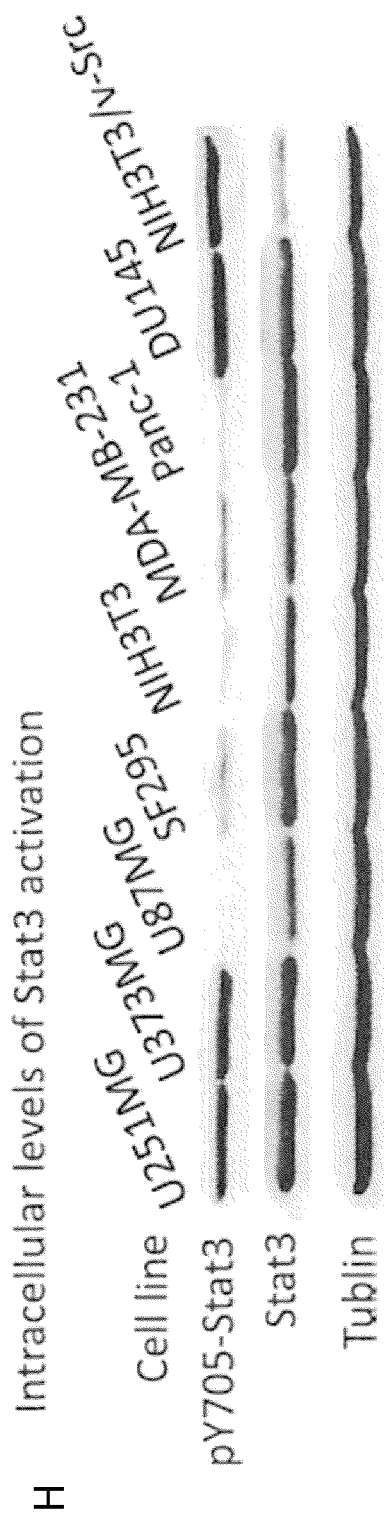
Figure 2:
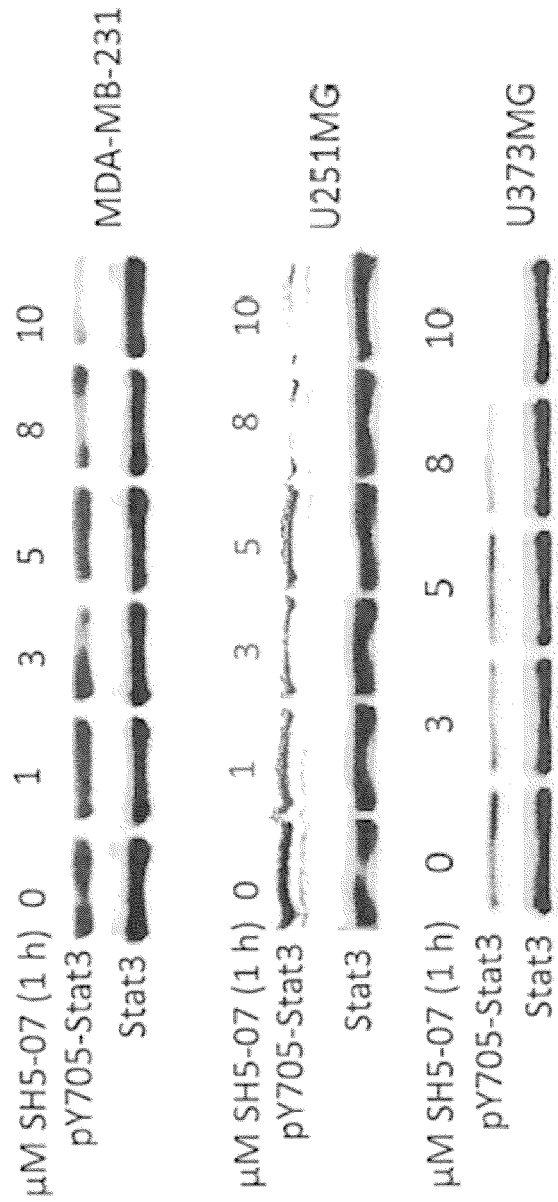
Figure 2:
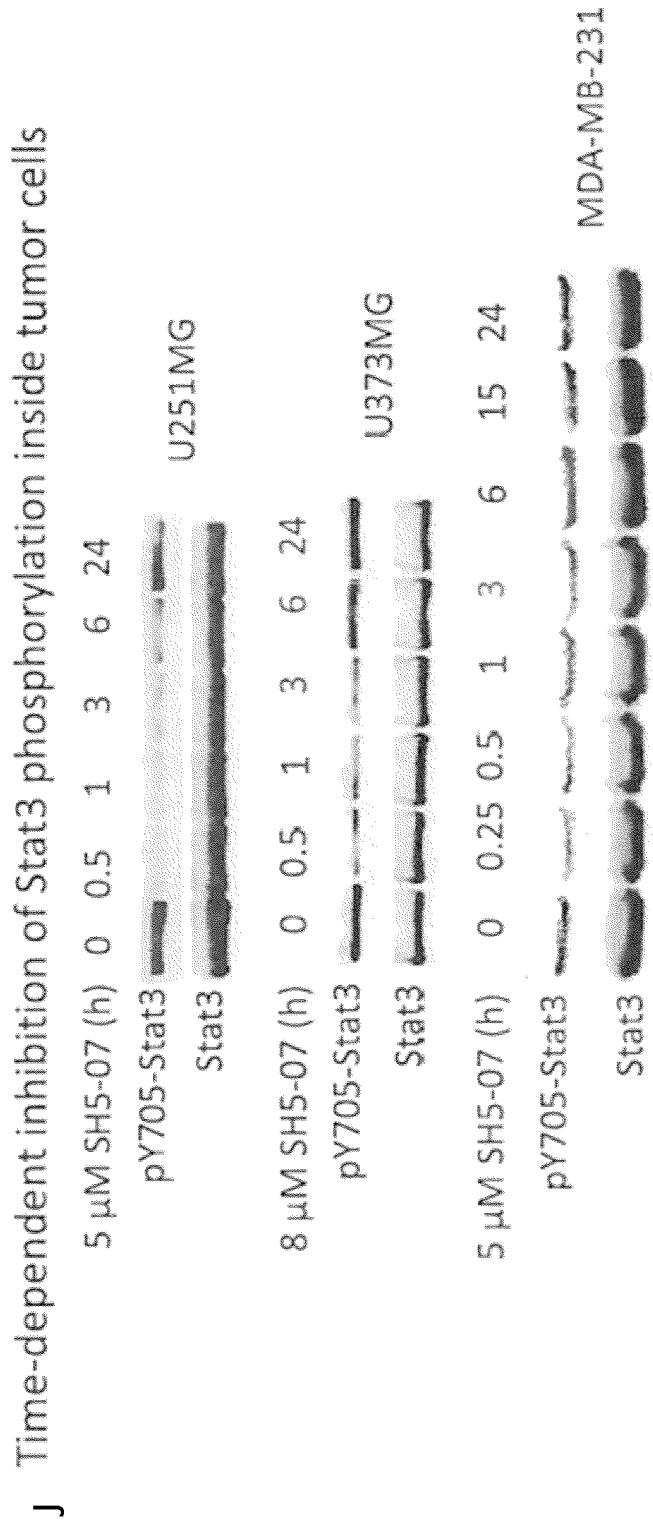

Stat3 is constitutively-activated in a variety of malignant cells, including human breast, glioma, prostate, and pancreatic cancer cells. Yue & Turkson, Targeting STAT3 in cancer: how successful are we?, Expert Opin Investig Drugs. 18:45-56 (2009); Turkson, STAT proteins as novel targets for cancer drug discovery, Expert Opin Ther Targets 8:409-422 (2004). EMSA analysis of nuclear extract preparations shows that treatment of human glioma (U251MG, and U373MG), breast (MDA-MB-231), non-small cell lung cancer (A549), prostate (DU145), and pancreatic cancer (Panc-1) cells, or v-Src-transformed mouse transformed fibroblasts (NIH3T3/v-Src) with SH5-07 or SH4-54 inhibits Stat3 DNA-binding activity in dose-(FIG. 2A) and time-dependent manner (FIG. 2B). Evidence of inhibition of constitutive Stat3 activity is seen at 1 µM concentration (FIG. 2A) and as early as 1 h treatment (FIG. 2B). In parallel, SDS-PAGE/Western blotting analysis of whole-cell lysates shows that similar treatment of U251MG, U373MG and MDA-MB-231 cells significantly blocked pY705Stat3 in time- and dose-dependent manner (FIGS. 2C and D). A rebound was observed in some instances in the Stat3 DNA-binding activity (FIG. 2B) and pY705Stat3 (FIG. 2D) at 6 h and thereafter. The mechanisms behind this observation are presently unclear and may in part be due to decreased intracellular levels of the compounds. However, immunoblotting analysis showed a sustained inhibition up to 9 h in U251MG cells treated once with 5 µM SH5-07 and re-dosed at 5 h (FIG. 2E).

Luciferase reporter studies were performed to further evaluate the effect of SH5-07 on Stat3 transcriptional activity in which normal mouse NIH3T3 fibroblasts were transiently co-transfected with the Stat3-dependent luciferase reporter, (pLucTKS3). and the vector encoding v-Src. Turkson et al., Novel peptidomimetic inhibitors of signal transducer and activator of transcription 3 dimerization and biological activity. Mol Cancer Ther 3:261-269 (2004); Turkson et al., Phosphotyrosyl peptides block Stat3-mediated DNA-binding activity, gene regulation and cell transformation. J. Biol. Chem. 276:45443-45455 (2001); Turkson et al., Stat3 activation by Src induces specific gene regulation and is required for cell transformation. Mol. Cell. Biol. 18:2545-2552 (1998); Turkson et al. (1999) Requirement for Ras/Rac1-Mediated p38 and c-Jun N-Terminal Kinase Signaling in Stat3 Transcriptional Activity Induced by the Src Oncoprotein. Mol. Cell. Biol. 19:7519-7528 (1999). The induction by v-Src of Stat3-specific luciferase reporter, pLucTKS3 (FIG. 2F (i), lanes 2 vs 1) was significantly (p<0.01) inhibited by the treatment with 3 or 5 µM SH5-07 (FIG. 2F(i), lanes 3 and 4 vs 2). By contrast, similar treatment of normal NIH3T3 fibroblasts transiently-co-transfected with the Stat3-independent luciferase reporter, pLucSRE and v-Src had no attenuating effect on the induction of pLucSRE (FIG. 2F(ii)). Turkson et al., Novel peptidomimetic inhibitors of signal transducer and activator of transcription 3 dimerization and biological activity, Mol Cancer Ther 3:261-269 (2004); Turkson et al., Stat3 activation by Src induces specific gene regulation and is required for cell transformation, Mol. Cell. Biol. 18:2545-2552 (1998); Turkson et al., Requirement for Ras/Rac1-Mediated p38 and c-Jun N-Terminal Kinase Signaling in Stat3 Transcriptional Activity Induced by the Src Oncoprotein. Mol. Cell. Biol. 19:7519-7528 (1999); Turkson et al., Phosphotyrosyl peptides block Stat3-mediated DNA-binding activity, gene regulation and cell transformation, J. Biol. Chem. 276:45443-45455 (2001). Furthermore, immunoblotting analysis showed that treatment of U251MG and MDA-MB-231 cells with SH5-07 at concentrations that inhibit Stat3 activation had little effects on pY1068EGFR, pY416Src, pJak2, pShc, pErk1/2, and pS473Akt or their expression levels (FIG. 2G). Accordingly, SH5-07 selectively inhibits constitutive activation of Stat3.

Example 3: Disputation of STAT3 Association with Growth Factor Receptor

To demonstrate that SH5-07 and SH4-54 inhibit Stat3 phosphorylation, the interaction between the EGF receptor and Stat3 was investigated by performing co-immunoprecipitation (co-IP) and immunoblotting analyses Immunoprecipitation from whole-cell lysates and SDS/PAGE and Western blotting analysis were performed as previously described. Turkson et al., Stat3 activation by Src induces specific gene regulation and is required for cell transformation. Mol. Cell. Biol, 18:2545-2552 (1998); Zhang et al., Activation of Stat3 in v-Src Transformed Fibroblasts Requires Cooperation of Jak1 Kinase Activity, J. Biol. Chem. 275:24935-24944 (2000). Primary antibodies used were anti-Stat3, pY705Stat3, pY416Src, Src, pErk1/2, Erk1/2, EGFR, pEGFR, pJAK2, c-Myc, Bcl-xL, Bcl-2, Survivin, and β-Actin (Cell Signaling, Danvers), and VEGF (Santa Cruz Biotech, Santa Cruz).

Figure 3:
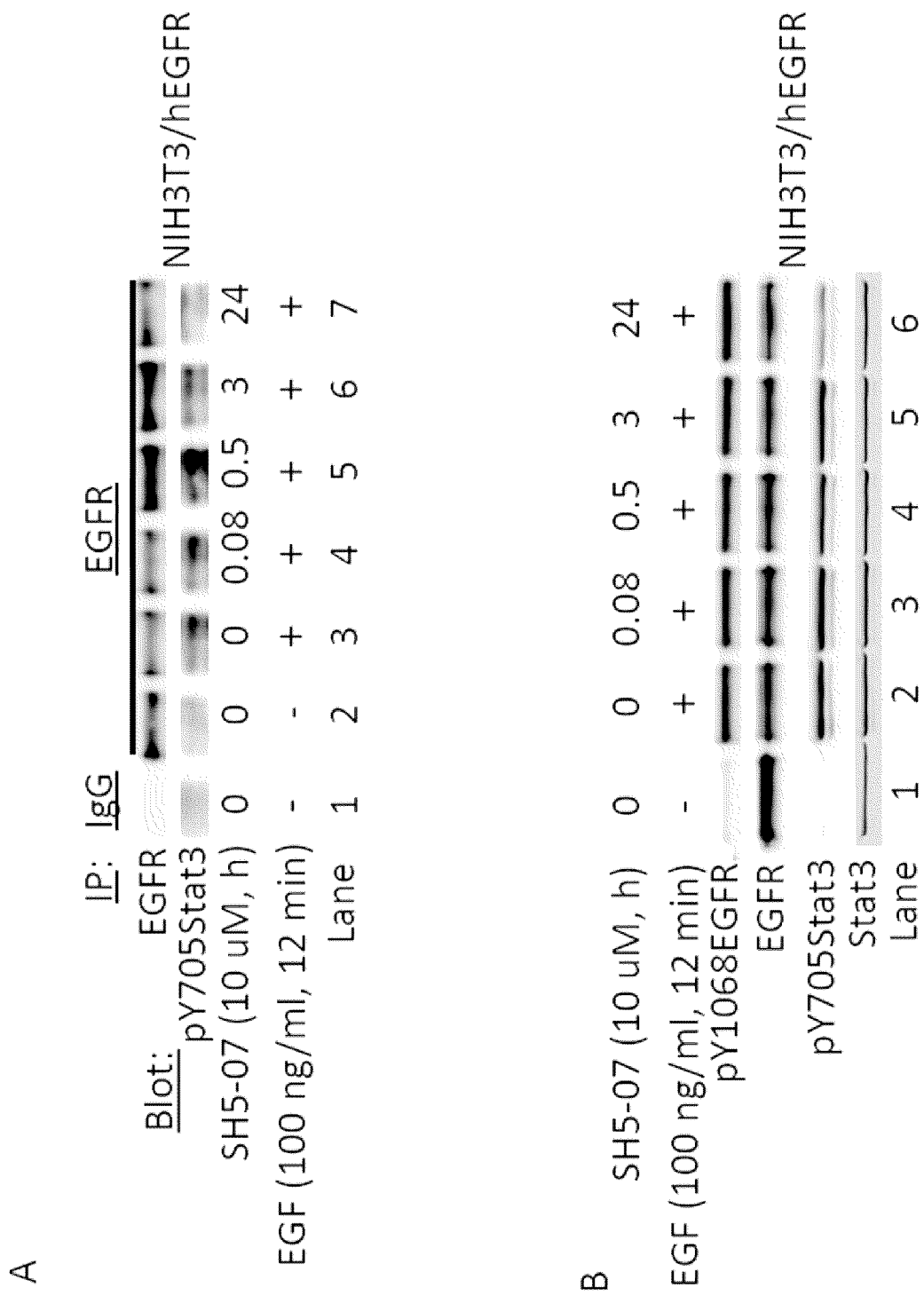
FIG. 3. SH5-07 disrupts Stat3 binding to EGFR and thereby inhibits EGF-induced Stat3 phosphorylation. (A and B), immunoblotting analysis of (A) immunecomplexes of EGFR or (B) whole-cell lysates prepared from NIH3T3/hEGFR cells unstimulated or stimulated with EGFR (100 ng/ml, 12 min) and untreated or treated with 10 μM SH5-07 for the indicated times and probing for pY1068EGFR, EGFR, pY705Stat3, or Stat3. Positions of proteins in gel are labeled; control lane (0) represents whole-cell lysates, or EGFR immunoprecipitates prepared from 0.05% DMSO-treated cells. Data are representative of 3-4 independent determinations.

In the resting mouse fibroblasts overexpressing EGF receptor (NIH3T3/EGFR), stimulation by EGF promoted the co-IP between EGF receptor and Stat3 (FIG. 3A, lanes 3-7 vs 2, pY705Stat3), which was suppressed by the pretreatment of cells with SH5-07 for 5 min to 24 h (FIG. 3A, lanes 7 vs 3). To further characterize the ability to effects of SH5-07, pY705Stat3 levels were probed under the same conditions, which showed that the induction of EGF receptor (FIG. 3B, lanes 2 vs 1, pY1068EGFR) lead to Stat3 phosphorylation (FIG. 3B, lanes 2 vs 1, pY705Stat3), which was inhibited when cells were pre-treated with SH5-07 for 24 h (FIG. 3B, lanes 6 vs 2, pY705Stat3). Combined together, these data showed that SH5-07 blocks the interaction of Stat3 with the EGF receptor, thereby inhibiting EGF/EGFR-induced de novo tyrosine phosphorylation of Stat3.

Example 4: SH5-07 and SH4-54 Block Growth, Viability, Survival, and the Migration of Cells Harboring Constitutively-Activated Stat3

Aberrantly-active Stat3 also promotes malignant cell proliferation and survival and malignant transformation. Yu et al., The STATS of Cancer-New molecular targets come of age. Nat. Rev. Cancer 4:97-105 (2004); Yue & Turkson (2009); Zhang et al. (2012); Zhang et al., A novel small-molecule disrupts Stat3 SH2 domain-phosphotyrosine interactions and Stat3-dependent tumor processes. Biochem Pharmacol 79:1398-409 (2010). Malignant cells were tested in viability assays for sensitivity to the Stat3 inhibitors.

The cell viability and proliferation assays were performed as described below. Cells in culture in 96-well plates were treated with or without SH5-07 or SH4-54 for 72 h and subjected to CyQuant cell proliferation assay (Invitrogen Corp/Life Technologies Corp, Carlsbad, Calif.). The colony survival assay was performed as previously reported. Zhang et al. (2012). Briefly, MDA-MB-231 or U251MG cells were seeded as single-cell in 6-cm dishes (500 cells per well), treated once the next day with SH5-07 for 48 h, and allowed to grow until large colonies were visible. Colonies were stained with crystal violet for 4 h and counted.

Figure 5:
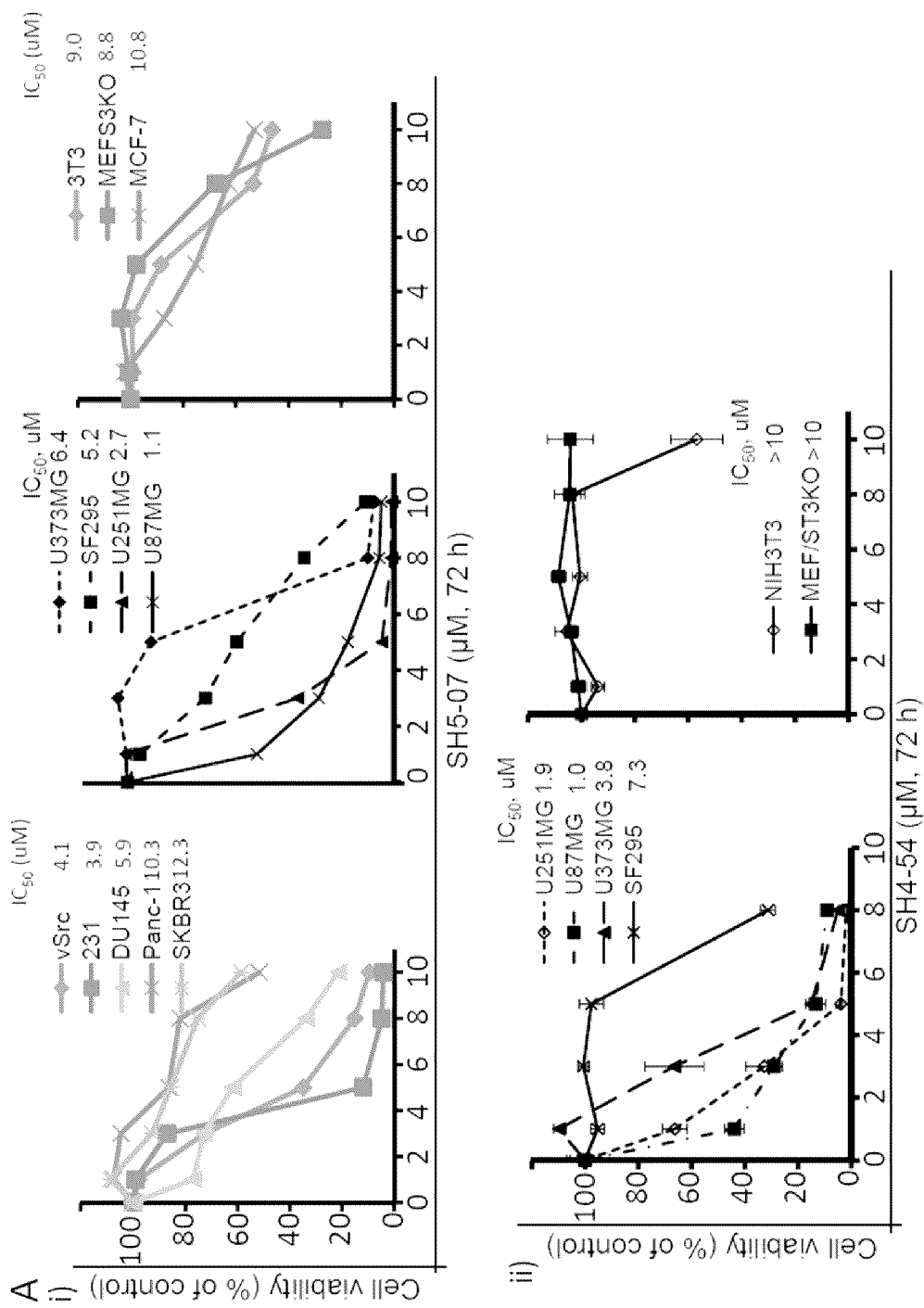
FIG. 5. SH5-07 and SH4-5 differentially suppress viability, growth, cell cycle, colony survival, and migration, and induce apoptosis of malignant cells harboring aberrant Stat3 activity. (A) Cultured human breast cancer cell lines (MDA-MB-231 and SKBR3), human prostate cancer cell line (DU145), and human pancreatic (Panc-1) cancer cell line, and human glioma (U373MG, SF295, U251MG and U87MG) cells that harbor varying degrees of constitutively-active Stat3 and normal mouse fibroblast, NIH3T3, Stat3 null mouse embryonic fibroblasts (Stat3−/−MEFs), and the human breast cancer MCF7 cell that do not express Stat 3 were treated once or untreated with 2-10 μM (i) SH5-07 or (ii) SH4-54 for 72 h. Cells were assayed for viability using CyQuant cell proliferation kit; (B) human breast cancer (MDA-MB-231) or glioma (U251MG) cells were seeded in culture and treated once with or without 5 or 8 μM SH5-07 for up to 96 h and cells were harvested at 24 h intervals for cell counting by trypan blue exclusion with phase-contrast microscopy; (C) human breast cancer (MDA-MB-231) and glioma (U251MG) cells were seeded as single-cell culture and treated once with 0-5 μM SH5-07 and allowed to culture until large colonies were visible, which were stained with crystal violet and enumerated; (D) cell cycle distribution analysis of human breast cancer, MDA-MB-231 or glioma U251MG cells treated or untreated with 3-8 μM SH5-07 for 24 or 48 h and processed by propidium iodide (PI) staining for flow cytometry analysis of DNA content; (E) Annexin V binding with PI staining in MDA-MB-231 or U251MG cells treated with or without 3-8 μM SH5-07 for 24 h and analyzed by flow cytometry; (F) soft agar colony formation assay and effects of daily treatment with 0-8 M of SH5-07 on MDA-MB-231 or U251MG; and (G) human breast cancer, MDA-MB-231 or glioma, U251MG cells were wounded and treated once with 8 μM SH5-07 for 22 h and allowed to migrate to the denuded area. IC$_{50}$ values were derived from graphical representation. Values are the mean and S.D. of 3-4 independent determinations. Data are representative of 3 independent determinations.
Figure 5:
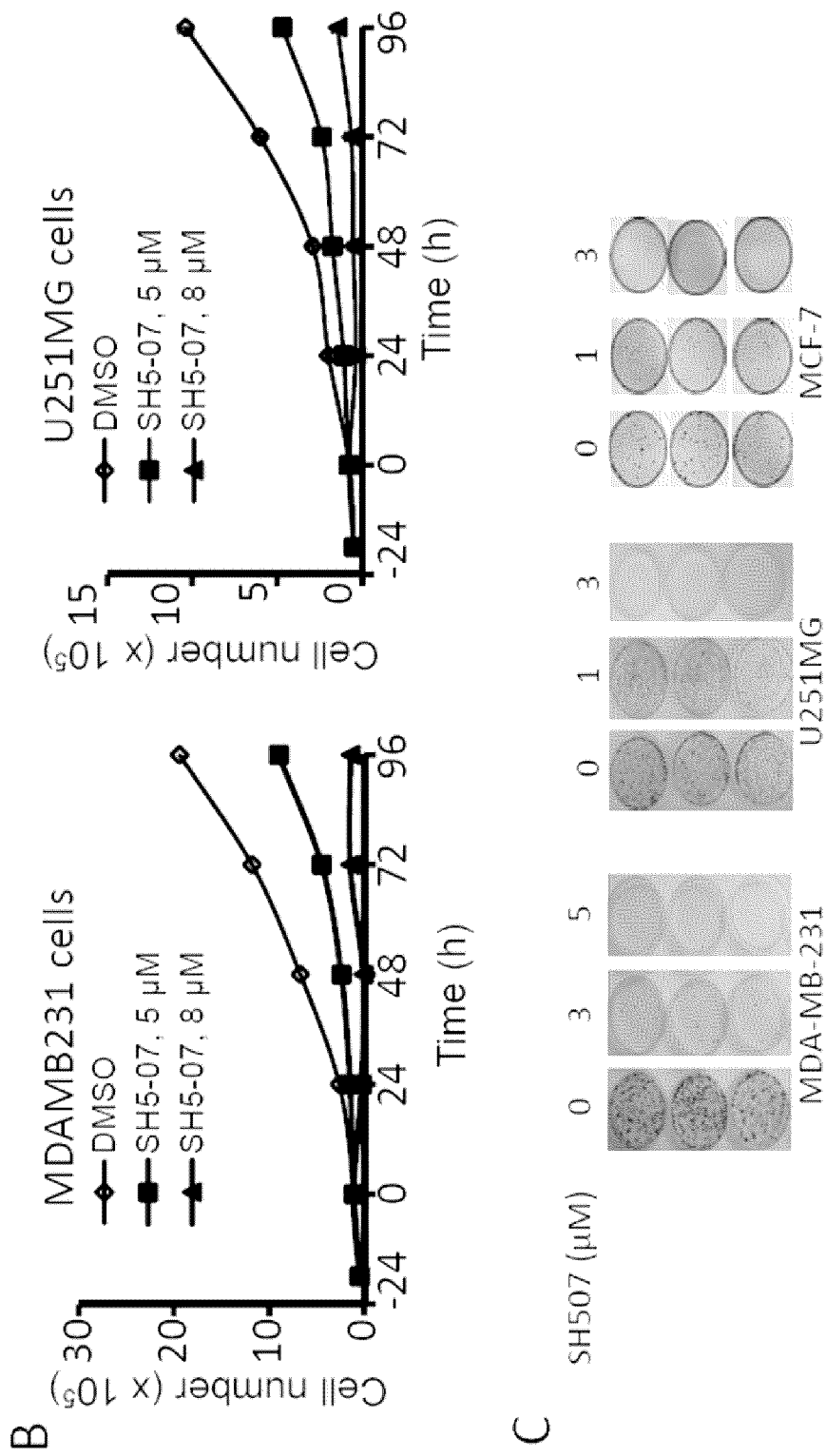
Figure 5:
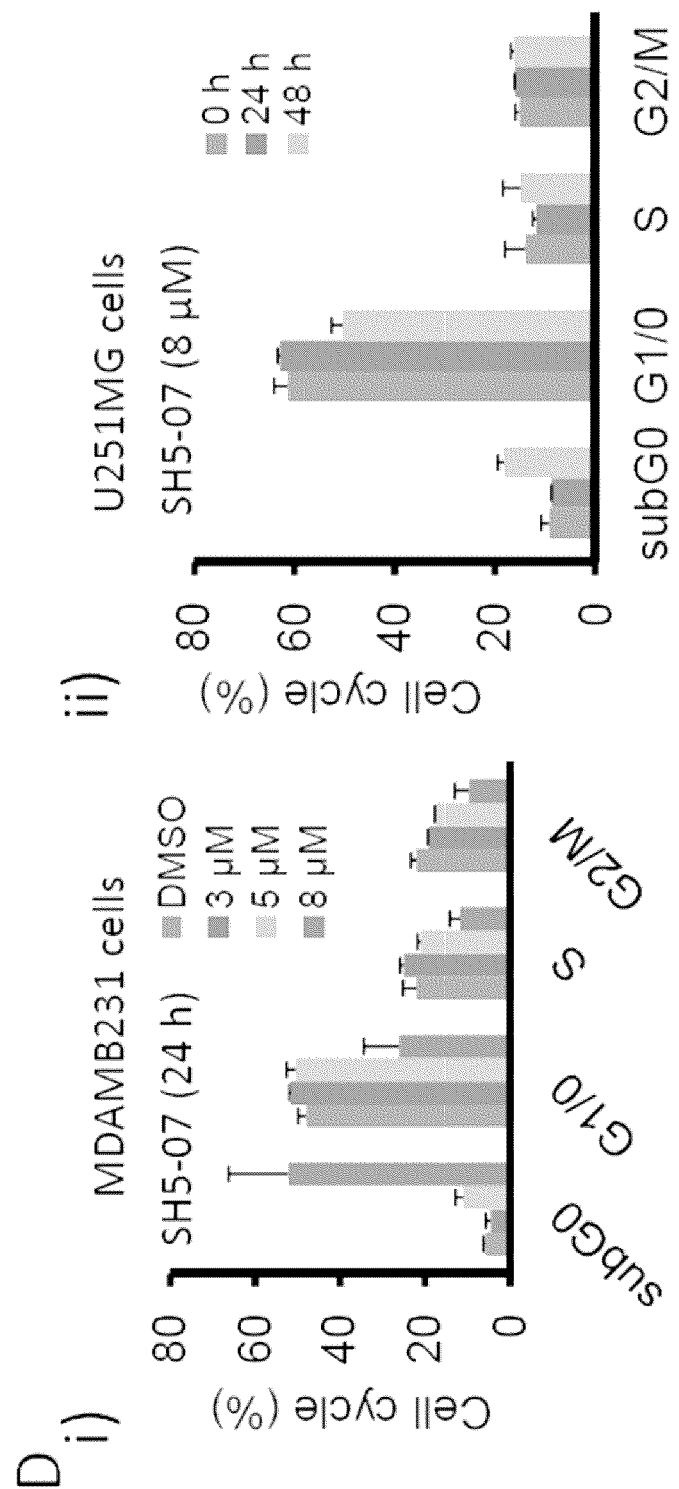
Figure 5:
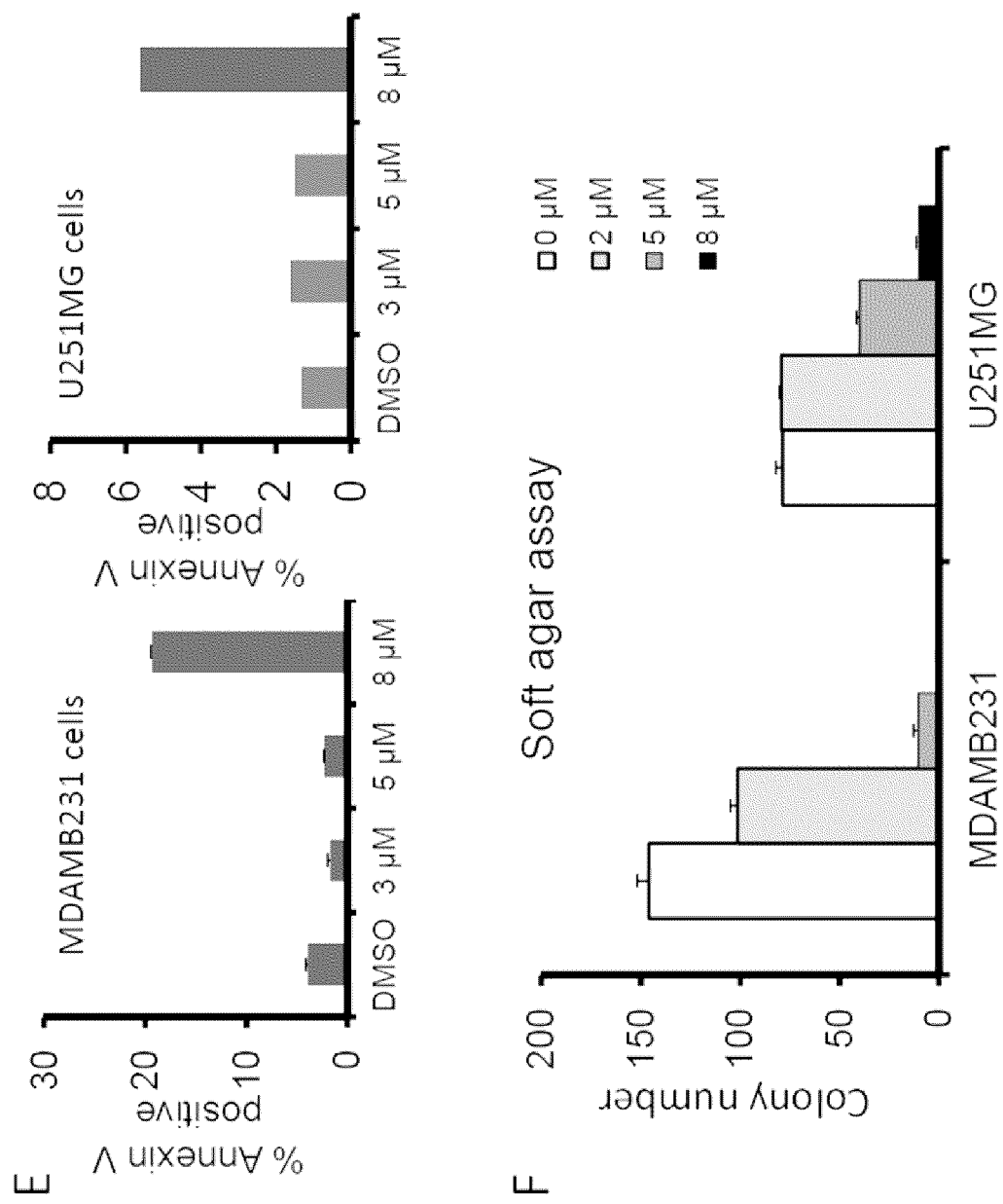
Figure 5:
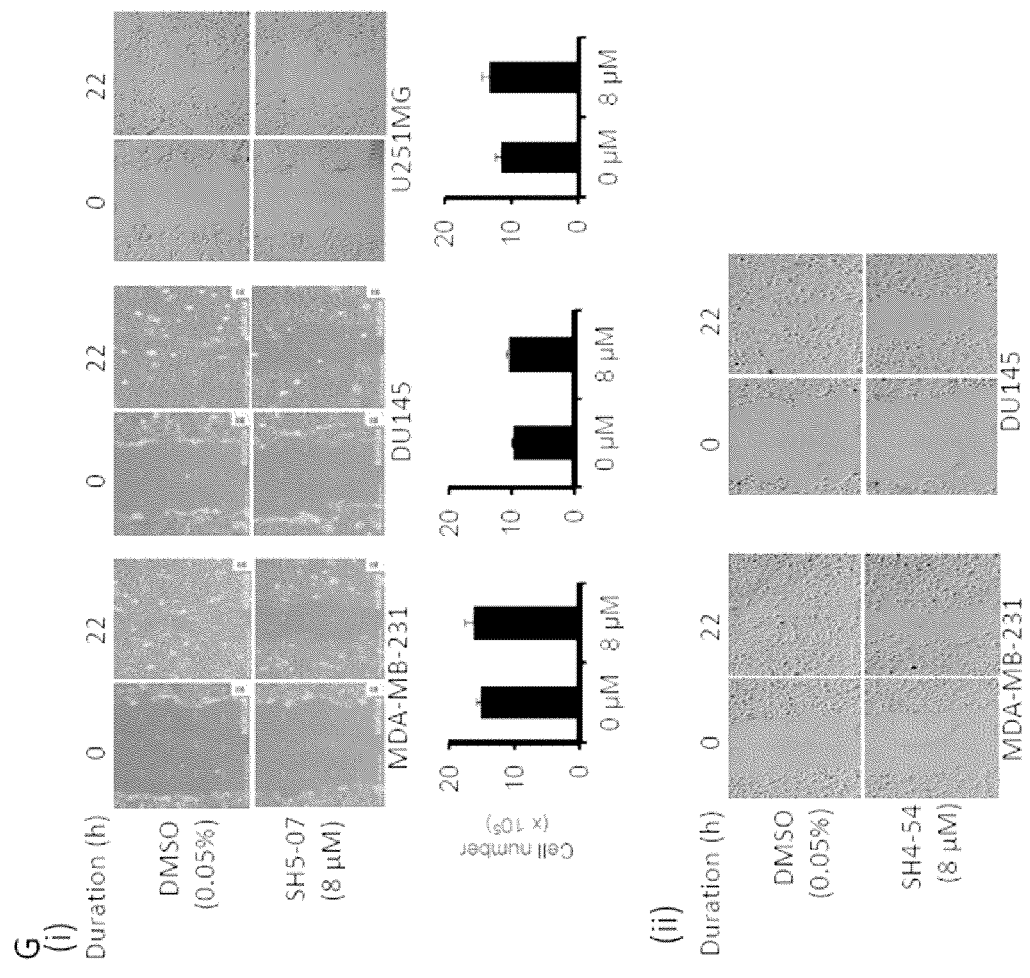
Figure 5:
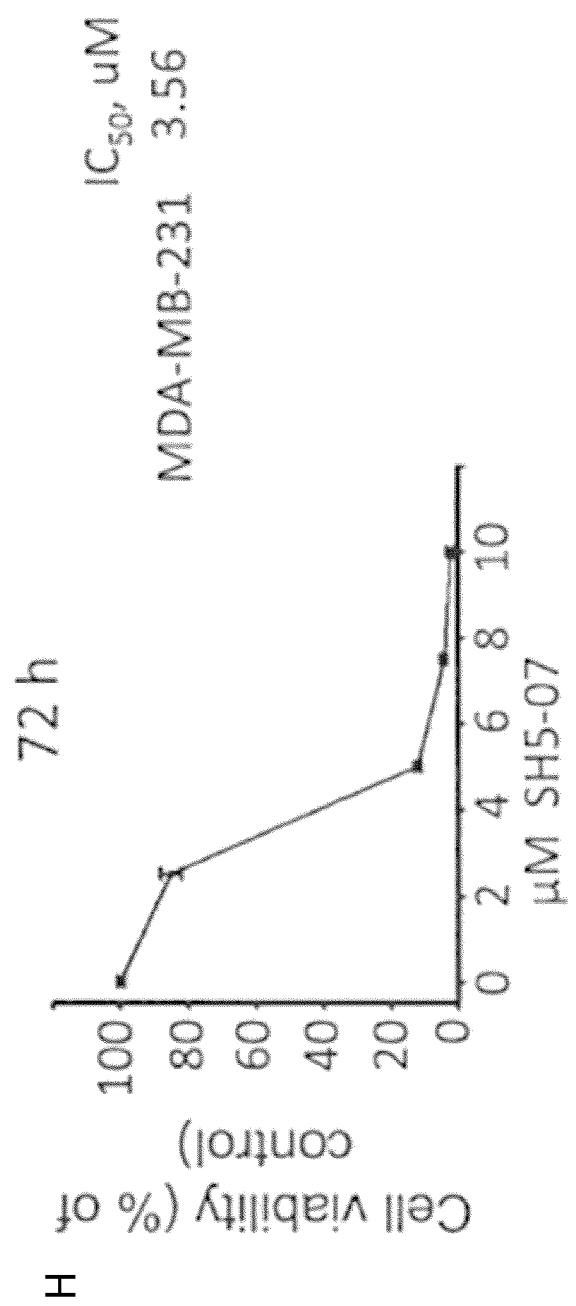
Figure 5:
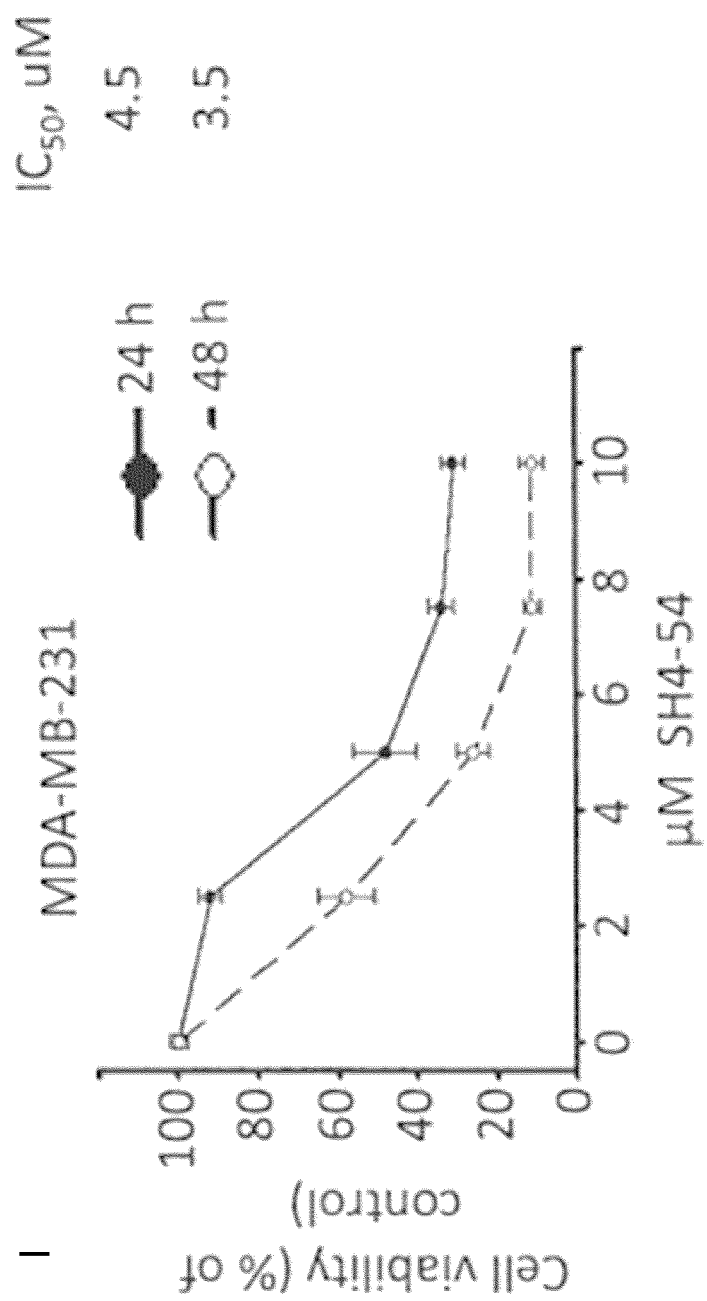

Treatment with increasing concentrations of SH5-07 or SH4-54 induced loss of viability, with $IC_{50}$ 1-3 µM for U251MG and U87MG (FIG. 5A), $IC_{50}$ 3-6.5 µM for glioma U373MG and SF295 lines, breast cancer cells, MDA-MB-231, prostate cancer DU145 cells, and v-Src-transformed fibroblasts, NIH3T3/v-Src (FIG. 5A), $IC_{50}$ of 10.3 µM for pancreatic cancer Panc-1 cells (FIG. 5A). By contrast, both agents weakly inhibited the viability of MCF-7, NIH3T3 and Stat3-null MEFs (Stat3–/–MEFs) cells that do not harbor aberrant Stat3 activity, with $IC_{50}$ 8.8-10.8 µM (FIG. 5A). The data showed that malignant cells harboring aberrantly-active Stat3 had variable sensitivities to SH5-07 and SH4-54. Notably, there was a correlation between the status of Stat3 activity of tumor cells, the inhibition of constitutively-active Stat3 in tumor cells, and the sensitivity of the viability of the malignant cells to SH5-07 or SH4-54 (FIGS. 2A-D, and 5). Consistent with this, viable cell counting by trypan blue exclusion with phase-contrast microscopy showed that treatment with SH5-07 preferentially suppressed growth of human glioma and breast cancer cells harboring aberrantly-active Stat3 in dose-dependent manner (FIG. 5B). These studies were extended to examine the effect of SH5-07 on anchorage-dependent and independent cell growth performed, as previously reported. See Zhang et al., A novel small-molecule disrupts Stat3 SH2 domain-phosphotyrosine interactions and Stat3-dependent tumor processes, Biochem Pharmacol 79:1398-409 (2010). Cultured single-cells were untreated or treated once with the agent and allowed to grow until large colonies were visible, which were stained and enumerated. Results showed a preferential suppression of the colony numbers of MDA-MB-231 and U251MG cells in clonogenic assay, which occurred in dose-dependent manner, compared to the effect on MCF-7 (FIG. 5C).

Example 5: SH5-07 and SH4-54 Block Stat3 Dependent Growth in a Wound Healing Assay Stat3 has a key role in cell cycle progression and cell survival, with the inhibition of constitutively-active Stat3 leading to cell growth arrest and apoptosis. Zhang et al. (2012); Niu et al., Roles of activated Src and Stat3 signaling in melanoma tumor cell growth, Oncogene 21:7001-7010 (2002). Cell cycle profile analysis by flow cytometry was performed to further study the effects of inhibitors on malignant cells. Treatment of malignant cells (MDA-MB-231 and U251MG) harboring aberrantly-active Stat3 with SH5-07 at 5-8 µM induced accumulation of cells in G0-G1 phase by 24 or 48 h (FIG. 5D), with decreases observed in cell populations in G1, S and G2/M phases in response to 8 µM treatment (FIG. 5D (i)). Furthermore, Annexin V staining and flow cytometry analysis showed that treatment with 8 µM SH5-07 induced significant apoptosis in both of MDA-MB-231 and U251MG cells (FIG. 5E). These data demonstrate that cell cycle blockage and apoptosis contributed to the loss of tumor cell viability induced by SH5-07. Soft agar colony formation assay also showed that treatment with SH5-07 induced a dose-dependent suppression of anchorage-independent growth of MDA-MB-231 and U251MG cells (FIG. 5F and Supplemental FIG. S2). These findings indicate that SH5-07 preferentially suppresses growth of malignant cells harboring aberrant Stat3.

To further investigate the ability of SH5-07 and SH4-54 to block Stat3-dependent tumor progression processes, a wound healing study was performed, as described herein. Wounds were made using pipette tips in monolayer cultures of cells in six-well plates. Cells were treated with or without increasing concentrations of SH5-07 and allowed to migrate into the denuded area for 12-24 hours. The migration of cells was visualized at a 10× magnification using an Axiovert 200 Inverted Fluorescence Microscope (Zeiss, Gottingen Germany), with pictures taken using a mounted Canon Powershot A640 digital camera (Canon USA, Lake Success, N.Y.). Cells that migrated into the denuded area were quantified.

Treatment with SH5-07 or SH4-54 for 22 h suppressed the numbers of MDA-MB-231, U251MG, U87MG, and DU145 cells migrating into the denuded area with minimum effects on cell viability (FIG. 5G). This supports that the compounds of this invention can inhibit cancer cell migration and metastasis.

Figure 6:
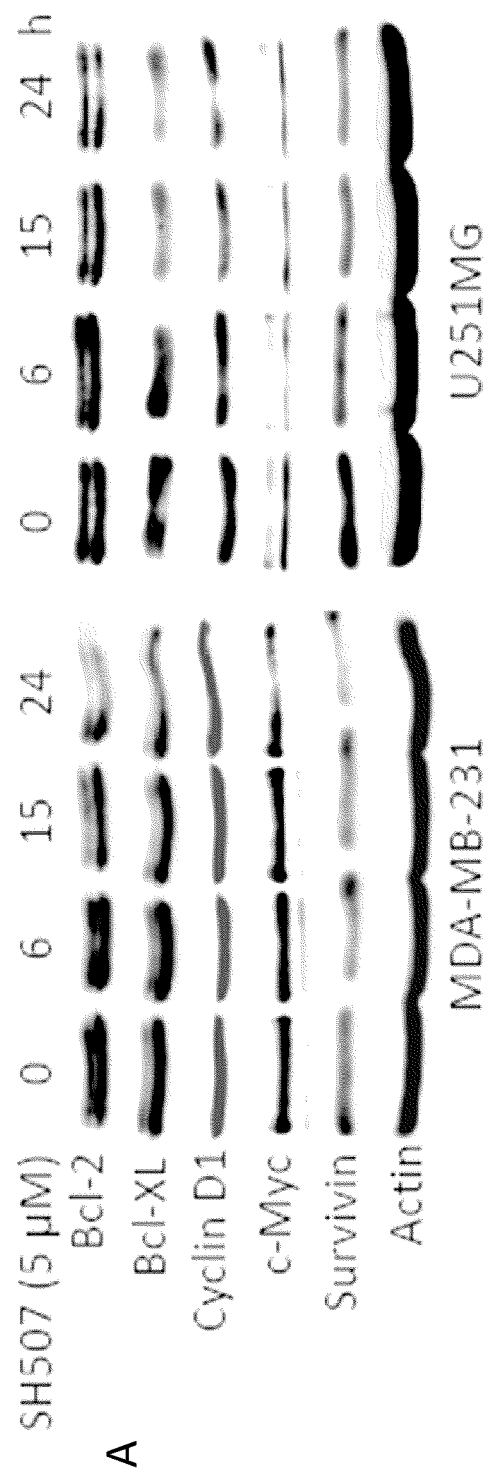
FIG. 6(A). SH5-07 suppresses Bcl-2, Bcl-xL, Cyclin D1, c-Myc, and Survivin expression. SDS-PAGE and Western blotting analysis of whole-cell lysates prepared from the human breast cancer MDA-MB-231 and glioma U251MG (DMSO, control) or treated with 5 micro Molar (uM) (SH-07 for 6-24 h and probing with anti-Bcl-2, Bcl-xL, Cyclin D1, c-Myc, and Survivin or β-actin antibodies. Positions of proteins in gel are shown. Data are representative of 3 independent determinations.
FIG. 6(B). SH5-07 inhibits FAK and IkBa phosphorylation. Another example using SDS-PAGE and Western blotting analysis of whole-cell lysates prepared from the human breast cancer MDA-MB-231 and U251MG cells untreated (DMSO, control) or treated with 5 micro Molar (uM) (SH507) for 6 to 24 hrs and probing with anti p-FAK, p-IkBa, IkBa antibodies. Positions of proteins in gel are shown.
Figure 6:
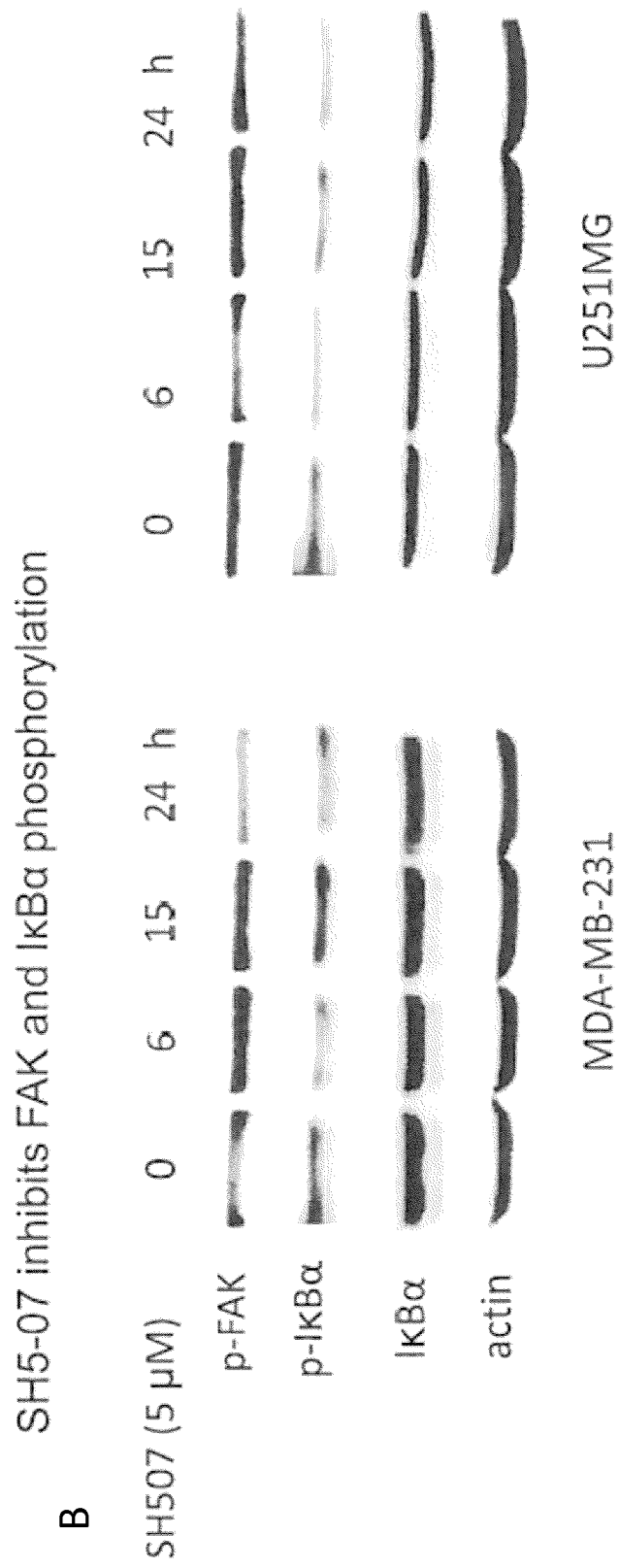

Example 6: SH5-07 Inhibits the Expression of c-Myc, Bcl-xL, Bcl-2, Cyclin D1, and Survivin Stat3 promotes the expression of known target genes, which are critical in the maintenance of the malignant phenotype. Yue & Turkson (2009); Turkson, STAT proteins as novel targets for cancer drug discovery, Expert Opin Ther Targets 8:409-422 (2004). In order to validate the inhibitory effect of SH5-07 on aberrant Stat3 signaling the expression of known Stat3 downstream target genes was determined. In the human breast cancer (MDA-MB-231) and glioma (U251) cell lines that harbor constitutively-active Stat3, further studies, including immunoblotting, and an analysis of whole-cell lysates showed that treatment with SH5-07 suppressed the induction of known Stat3-regulated genes, e.g., Bcl-2, Bcl-xL, Cyclin D1, c-Myc, and Survivin, which were significantly suppressed in response to 24 h-treatment (FIG. 6). These data demonstrate that SH5-07 sufficiently represses the constitutive induction of Stat3-regulated genes, thereby blocking the dysregulation of growth and survival promoted by aberrantly-active Stat3.

Example 7: Demonstration of Efficacy and Safety: SH5-07 Suppresses Growth of Human Breast Tumor and Glioma Xenografts in Mice The efficacy of SH5-07 in the treatment of human breast and glioma, using a mouse xenograft model was demonstrated. These studies showed that administering SH5-07 inhibited the growth of mouse subcutaneous xenografts of human breast tumor (MDA-MB-231) that harbor aberrant Stat3 activity, when delivered via oral gavage at a dose of 3 mg/kg every day (FIG. 7A).

To perform these studies, six-week-old female athymic nude mice were purchased from Harlan and maintained in the institutional animal facilities approved by the American Association for Accreditation of Laboratory Animal Care. Athymic nude mice were injected subcutaneously in the left flank area with 5×10⁶ human breast cancer U251MG cells in 100 μL of PBS. When tumors of a diameter of 3 mm were established, animals were grouped so that the mean tumor sizes in all groups were nearly identical, then given SH5-07 oral at 3 mg/kg every day for 27 days and monitored every 2 or 3 days, and tumor sizes were measured with calipers. Tumor volume was calculated according to the formula $V=0.52 \times a^2 \times b$, where a, smallest superficial diameter, b, largest superficial diameter. For each treatment group, the tumor volumes for each set of measurements were statistically analyzed in comparison to the control (non-treated) group. Statistical analysis-Statistical analysis was performed on mean values using Prism GraphPad Software, Inc. (La Jolla, Calif.). The significance of differences between groups was determined by the paired t-test at $p<0.05^*$, $<0.01^{}$, and $<0.001^{*}$.

Figure 7:
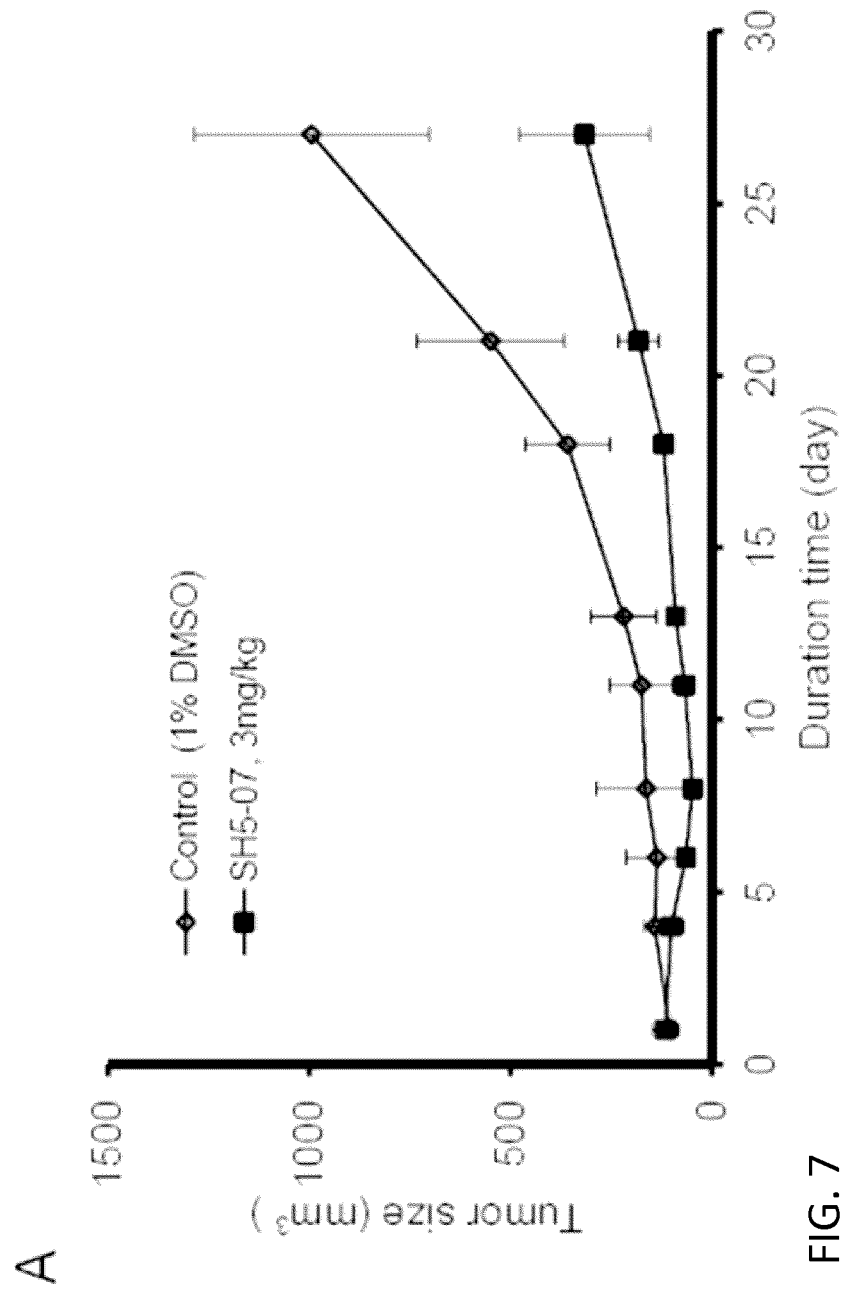
FIG. 7. Antitumor effects against human glioma tumor xenografts and in vivo pharmacokinetic properties of SH5-07. (A) Mice bearing U251MG subcutaneous tumor xenografts were administered SH5-07 via oral gavage, 3 mg/kg or vehicle (0.05% DMSO) every day for the indicated time. Tumor sizes, measured every 2 or 3 days were converted to tumor volumes and plotted against days of treatment; and (B) graphical representations of SH5-07 levels analyzed in (i) plasma or (ii) tumor tissue samples collected from mice at 0, 10 or 60 min post single dosing of 3 mg/kg via oral gavage. Values, mean±S.D., n=6.
Figure 7:
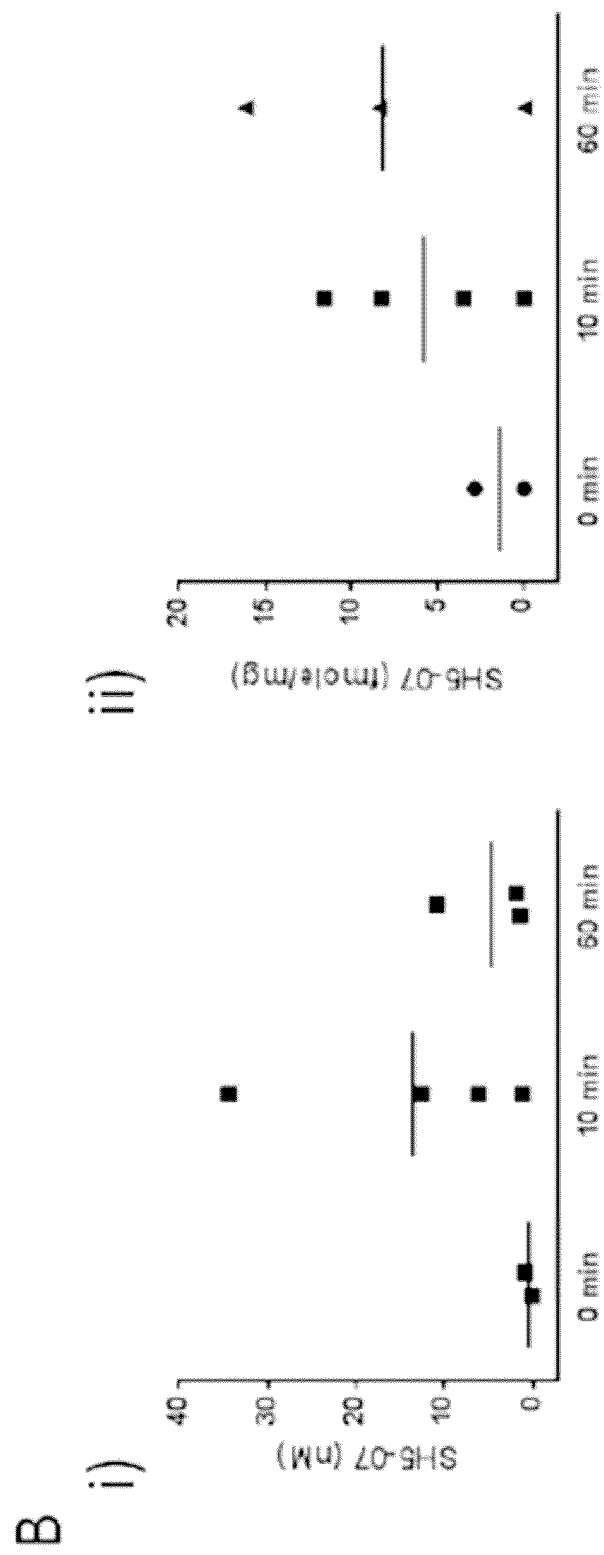
Figure 8:
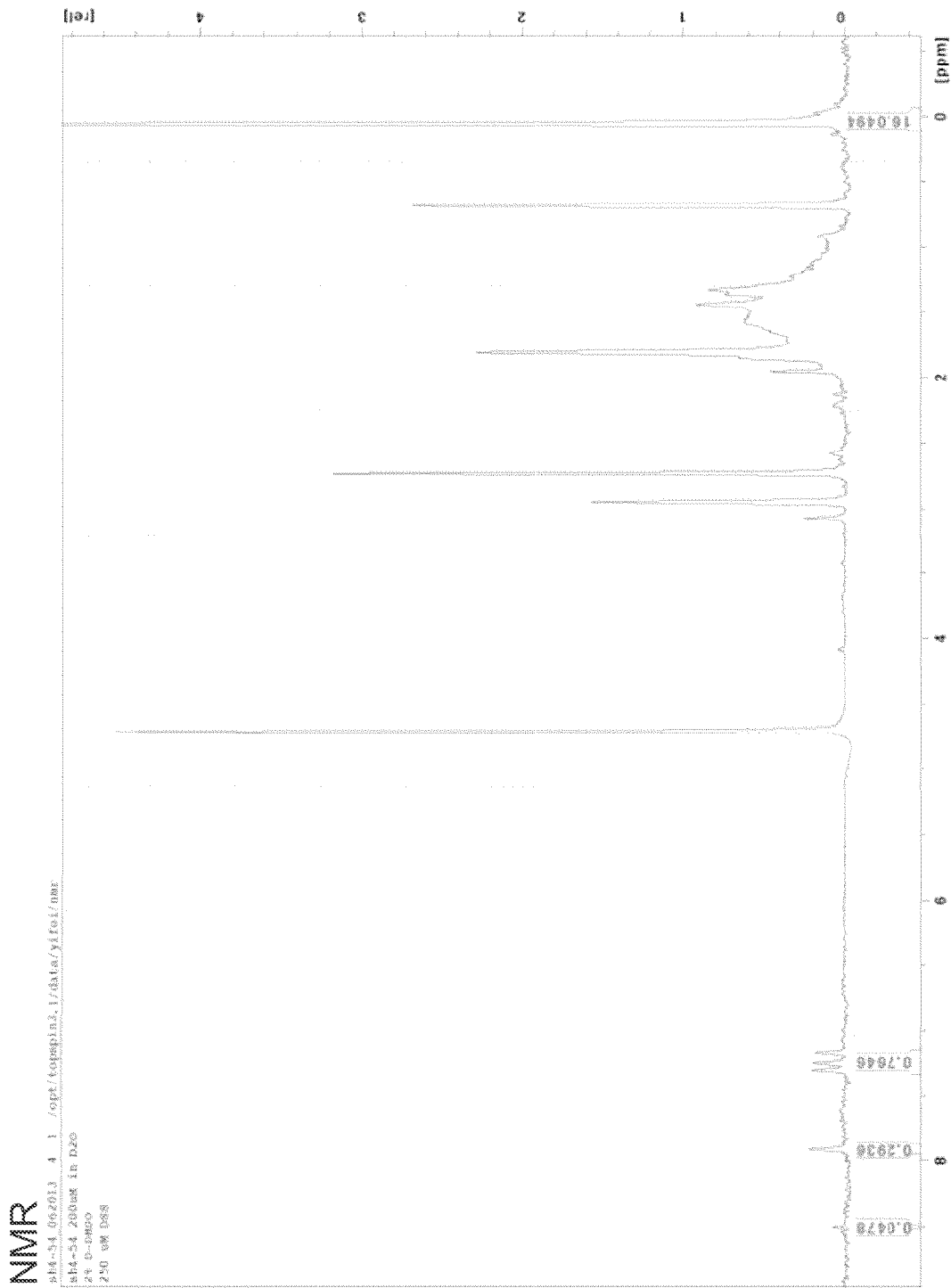
FIG. 8. Structure and predicted NMR chemical shifts of SH4-54 and NMR spectra of 200 μM SH4-54 in solution. When intended to make 200 uM concentration solution, precipitation was observed and the signal of approximately 20 uM compound was observed.
Figure 9:
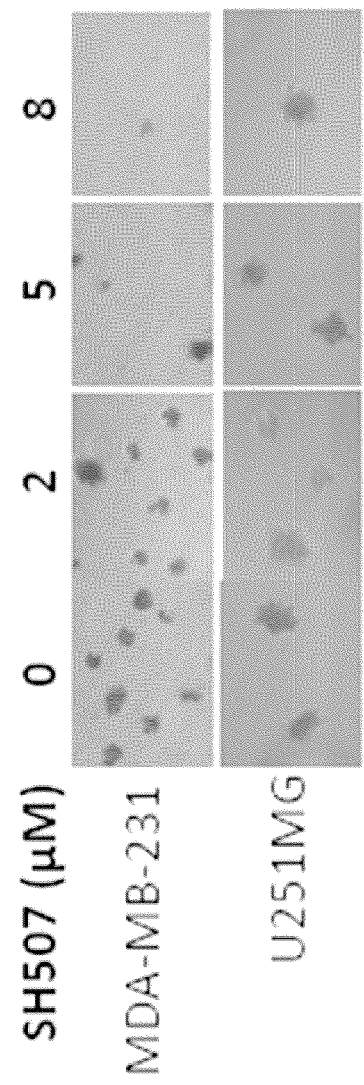
FIG. 9. Colony survival assay and the effects of SH5-07 on MDA-MB-231 or U251MG cells.

The results demonstrated that administering SH5-07 inhibited the growth of the human breast tumor (MDA-MB-231) grafts that harbor aberrant Stat3 activity (FIG. 7A). No significant changes in body weights or obvious signs of toxicity, such as loss of appetite, decreased activity, or lethargy, were observed during the study.

Example 8: Determination of Intracellular and Tissue Levels, and Pharmacokinetics Following Administration of SH5-07

The intracellular and tissue levels of SH5-07 were studied, following a single treatment. U251 cells in culture were treated once with 5 μM SH5-07, and at 1, 6, and 24 h thereafter, cell extracts were prepared for LC-MS analysis for levels of agent. The results showed intracellular levels of SH5-07 of 1,238±181 μM at 1 h, which dramatically diminished to 27.6 μM at 6 h and to background levels at 24 h (Table 1). This data shows that SH55-07 is orally available, at levels sufficient to inhibit Stat3 activity.

Moreover, in vivo pharmacokinetic analysis of SH5-07 was performed by collecting serum and brain tissue samples from untreated mice or from treated mice at 10 and 60 min after a single dose of tail vein injection of SH5-07 (3 mg/kg). The results (FIG. 7B) showed that the average level of SH5-07 in serum was 13.54 μM at 10 min post-dosing, which declined by 60 min to 4.67 μM, whereas the corresponding average levels in the brain tissue were 7.76 and 8.19 fmole/mg tissue, respectively.

Example 8: Treatment of Cancer

Subjects with glioma, breast cancer or pancreatic cancer are treated by intravenous or oral administration of SH5-07 at a dose of between 0.08 mg/kg to 0.4 mg/kg, with additional doses administered as needed. The condition of the subjects are monitored, and the shrinkage of the tumors, or slowing of the progession of tumor growth is observed. The results indicate and confirm the surprising efficacy of the exemplary Stat 3 inhibitors of the present disclosure.

Patents, patent applications, publications, scientific articles, books, web sites, and other documents and materials referenced or mentioned herein are indicative of the levels of skill of those skilled in the art to which the inventions pertain. Each such referenced document and material is hereby incorporated by reference to the same extent as if it had been incorporated by reference in its entirety individually or set forth or reprinted herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above, including, but not limited to, any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing, or optionally allowing the removal of, any subject matter from the genus, regardless of whether or not the excised materials, or options, were specifically recited or identified in haec verba herein, and all such variations form a part of the original written description of the inventions. In addition, where features, or aspects, of an invention are described in terms of a Markush group, the invention shall be understood thereby to be described in terms of each and every, and any, individual member or subgroup of members of the Markush group.

Although the invention has been described in terms of synthesis of GGCIs and GGCI salts, it should be recognized that the routes, steps, and intermediates described in the disclosure are applicable to the synthesis of CGI.

The inventions illustratively described and claimed herein can suitably be practiced in the absence of any element or elements, limitation or limitations, not specifically disclosed herein, or described herein, as essential. Thus, for example, the terms "comprising," "including," "containing," "for example", etc., shall be read expansively and without limitation. The term "including" means "including but not limited to." The phrase "for example" is not limited to, or by, the items that follow the phrase. All references to things "known in the art" include all those things and equivalents and substitutes, whether now known, or later discovered.

In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

The methods and processes illustratively described herein may be suitably practiced in differing orders of steps. They are not necessarily restricted to the orders of steps indicated herein, or in the claims.

Under no circumstances may the patent be interpreted to be limited to the specific examples, or embodiments, or methods, specifically disclosed herein. Under no circumstances may the patent be interpreted to be limited by any statement made by any Examiner, or any other official or employee of the Patent and Trademark Office, unless such statement was specifically, and without qualification or reservation, expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary of, and not intended as limitations on, the scope of the invention. Other objects, aspects, and embodiments will occur to those skilled in the art upon consideration of this specification, and are encompassed within the spirit of the invention as defined by the scope of the claims. Where examples are given, the description shall be construed to include, but not to be limited to, only those examples. It will be readily apparent to one skilled in the art that varying substitutions and modifications may be made to the invention disclosed herein, without departing from the scope and spirit of the invention, and from the description of the inventions, including those illustratively set forth herein, it is manifest that various modifications and equivalents can be used to implement the concepts of the present invention, without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

While this invention has been disclosed with reference to specific embodiments, it is apparent that other embodiments and variations of this invention can be devised by those skilled in the art, without departing from the true spirit and scope of the invention. The appended claims include all such embodiments and equivalent variations.

We claim:

1. A pharmaceutical composition comprising a pharmaceutically effective amount of a dosage of 0.05 mg/kg to 4 mg/kg of a compound, or salt, of Formula II

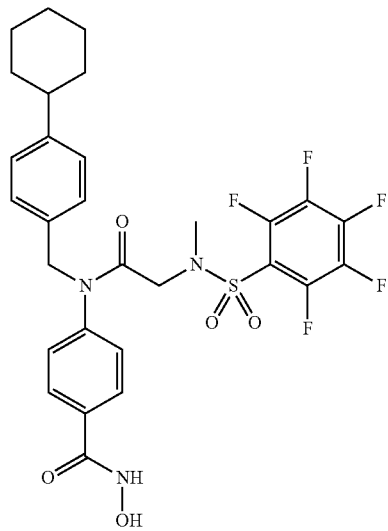 [SMILES: CN(CC(=O)N(Cc1ccc(C2CCCCC2)cc1)c1ccc(C(=O)NO)cc1)S(=O)(=O)c1c(F)c(F)c(F)c(F)c1F]

and a pharmaceutically acceptable excipient.

2. A method of treating cancer harboring constitutively active Stat3 activity, comprising administering to a subject in need thereof, a therapeutically effective amount of a pharmaceutical composition comprising the composition of claim 1.

3. The method of claim 2, wherein the effective dose of the composition of claim 1 is from about 0.08 mg/kg to about 0.5 mg/kg, from about 0.08 to about 0.24 mg/kg, or from about 0.24 to about 0.5 mg/kg, or from about 0.08 to 0.5 mg/kg.

```
                            SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
agcttcattt cccgtaaatc ccta                                             24

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
agatttctag gaattcaa                                                    18
```

4. The method of claim 2, wherein the one or more effective doses of the composition of claim 1 are administered orally.

5. The method of claim 2, wherein the one or more effective doses of the composition of claim 1 are administered subcutaneously, intravenously, or intramuscularly.

6. The method of claim 2, wherein the cancer is a solid tumor.

7. The method of claim 6, wherein the solid tumor comprises glioma, breast cancer or pancreatic cancer.

8. The method of claim 2, wherein the cancer is selected from the group consisting of: lung, breast, prostate, pancreatic, ovarian, bladder, head and neck, thyroid, brain, skin and kidney.

9. The method of claim 2, wherein the cancer is selected from the group consisting of: brain tumors, gliomas, medulloblastomas, cerebral menangiomas, breast, prostate, pancreatic, ovarian, bladder, head and neck, malignant melanoma, multiple myeloma, lymphomas, including anaplastic large T cell lymphoma, sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous lekemia (CML), megakaryocytic leukemia, and large granula lymphocyte (LGL) leukemia, thyroid, skin, lung, or kidney cancer, renal cell carcinoma, pancreatic adenocarcinoma, ovarian carcinoma, squamous cell carcinoma of the head and neck, or Hodgkin's Lymphoma.

10. The method of claim 2, wherein each dose of the composition of claim 1 is between about 0.08 mg/kg and less than about 0.5 mg/kg, and said dose is administered by a delivery route selected from the group consisting of oral, intradermal, intramuscular, intraperitoneal, intravenous, topical, subcutaneous, and epidural routes.

11. The method of claim 6, whereby tumor progression is inhibited, or reduced, or multi-drug resistance (MDR) is inhibited or reduced.

* * * * *